United States Patent
Saim et al.

(10) Patent No.: US 9,968,598 B2
(45) Date of Patent: *May 15, 2018

(54) PROCESS OF MAKING STABLE ABUSE-DETERRENT ORAL FORMULATIONS

(71) Applicant: Collegium Pharmaceutical, Inc., Canton, MA (US)

(72) Inventors: Said Saim, Wrentham, MA (US); Alison B. Fleming, Mansfield, MA (US); Ravi K. Varanasi, Walpole, MA (US)

(73) Assignee: Collegium Pharmaceutical, Inc., Canton, MA (US)

( * ) Notice: Subject to any disclaimer, the term of this patent is extended or adjusted under 35 U.S.C. 154(b) by 0 days. days.

This patent is subject to a terminal disclaimer.

(21) Appl. No.: 15/649,024

(22) Filed: Jul. 13, 2017

(65) Prior Publication Data

US 2017/0368057 A1    Dec. 28, 2017

Related U.S. Application Data

(63) Continuation of application No. 15/255,859, filed on Sep. 2, 2016, now Pat. No. 9,737,530.
(Continued)

(51) Int. Cl.
| | | |
|---|---|---|
| *A61K 31/48* | (2006.01) | |
| *A61K 31/485* | (2006.01) | |
| *A61K 47/12* | (2006.01) | |
| *A61K 47/44* | (2017.01) | |
| *A61K 47/26* | (2006.01) | |

(Continued)

(52) U.S. Cl.
CPC .......... *A61K 31/485* (2013.01); *A61K 9/1617* (2013.01); *A61K 9/1694* (2013.01); *A61K 9/4808* (2013.01); *A61K 9/4833* (2013.01); *A61K 9/4858* (2013.01); *A61K 9/4875* (2013.01); *A61K 47/12* (2013.01); *A61K 47/26* (2013.01); *A61K 47/44* (2013.01)

(58) Field of Classification Search
None
See application file for complete search history.

(56) References Cited

U.S. PATENT DOCUMENTS

| | | | |
|---|---|---|---|
| 2,404,319 | A | 7/1946 | Shelton |
| 3,015,128 | A | 1/1962 | Somerville, Jr. |

(Continued)

FOREIGN PATENT DOCUMENTS

| | | | |
|---|---|---|---|
| CA | 2273808 | A1 | 9/2000 |
| EP | 0179583 | A1 | 4/1986 |

(Continued)

OTHER PUBLICATIONS

"Castor oil, hydrogenated," European Pharmacopoeia V.5, p. 1197-1198 (2005).

(Continued)

*Primary Examiner* — Robert A Wax
*Assistant Examiner* — Melissa S Mercier
(74) *Attorney, Agent, or Firm* — Cooley LLP

(57) ABSTRACT

The present disclosure relates to cured pharmaceutical compositions designed to reduce the potential for improper administration of drugs that are subject to abuse, the process of curing such composition in order to improve the dissolution stability, method of using the same for treatment of pain.

30 Claims, 11 Drawing Sheets

Related U.S. Application Data

Figure 1:
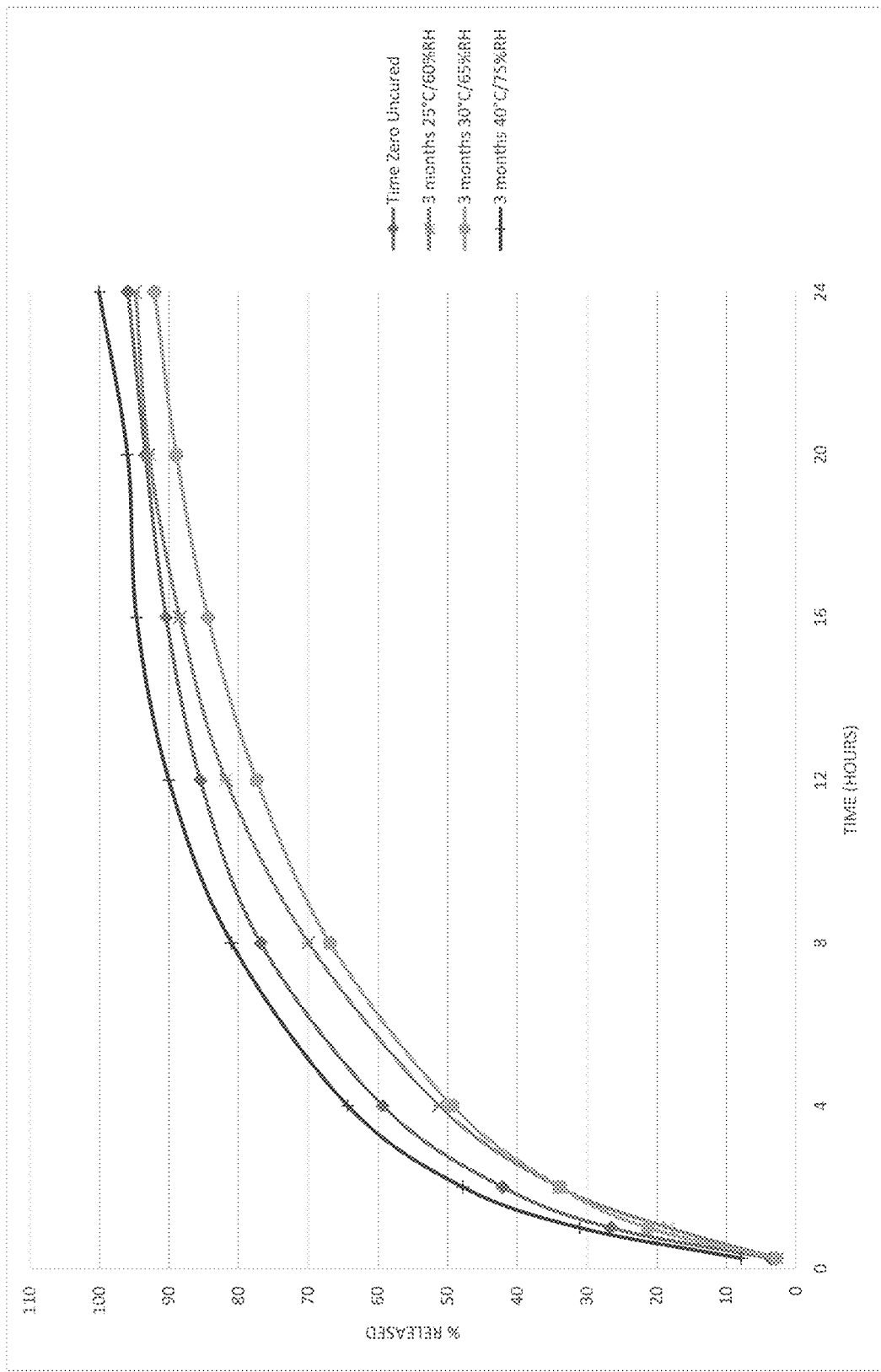

(60) Provisional application No. 62/353,839, filed on Jun. 23, 2016.

(51) Int. Cl.
 A61K 9/48 (2006.01)
 A61K 9/16 (2006.01)

(56) References Cited

U.S. PATENT DOCUMENTS

| | | | |
|---|---|---|---|
| 3,146,167 A | 8/1964 | Lantz, Jr. et al. |
| 3,172,816 A | 3/1965 | Swintosky et al. |
| 3,336,200 A | 8/1967 | Krause et al. |
| 3,773,955 A | 11/1973 | Pachter et al. |
| 3,966,940 A | 6/1976 | Pachter et al. |
| 3,980,766 A | 9/1976 | Shaw et al. |
| 4,070,494 A | 1/1978 | Hoffmeister et al. |
| 4,457,933 A | 7/1984 | Gordon et al. |
| 4,569,937 A | 2/1986 | Baker et al. |
| 4,599,326 A | 7/1986 | Marvola et al. |
| 4,675,140 A | 6/1987 | Sparks et al. |
| 4,722,941 A | 2/1988 | Eckert et al. |
| 4,861,598 A | 8/1989 | Oshlack |
| 4,869,904 A | 9/1989 | Uekama et al. |
| 5,190,947 A | 3/1993 | Riess et al. |
| 5,356,467 A | 10/1994 | Oshlack et al. |
| 5,460,826 A | 10/1995 | Merrill et al. |
| 5,508,042 A | 4/1996 | Oshlack et al. |
| 5,639,476 A | 6/1997 | Oshlack et al. |
| 5,656,295 A | 8/1997 | Oshlack et al. |
| 5,700,410 A | 12/1997 | Nakamichi et al. |
| 5,756,123 A | 5/1998 | Yamamoto et al. |
| 5,756,483 A | 5/1998 | Merkus |
| 5,849,240 A | 12/1998 | Miller et al. |
| 5,866,161 A | 2/1999 | Childers et al. |
| 5,891,471 A | 4/1999 | Miller et al. |
| 5,914,129 A | 6/1999 | Mauskop |
| 5,952,005 A | 9/1999 | Olsson et al. |
| 5,958,452 A | 9/1999 | Oshlack et al. |
| 5,958,459 A | 9/1999 | Chasin et al. |
| 5,965,161 A | 10/1999 | Oshlack et al. |
| 5,965,163 A | 10/1999 | Miller et al. |
| 5,968,551 A | 10/1999 | Oshlack et al. |
| 6,048,736 A | 4/2000 | Kosak |
| 6,068,855 A | 5/2000 | Leslie et al. |
| 6,103,261 A | 8/2000 | Chasin et al. |
| 6,156,764 A | 12/2000 | Asmussen et al. |
| 6,162,467 A | 12/2000 | Miller et al. |
| 6,248,363 B1 | 6/2001 | Patel et al. |
| 6,255,502 B1 | 7/2001 | Penkler et al. |
| 6,261,599 B1 | 7/2001 | Oshlack et al. |
| 6,277,384 B1 | 8/2001 | Kaiko et al. |
| 6,290,990 B1 | 9/2001 | Grabowski et al. |
| 6,294,195 B1 | 9/2001 | Oshlack et al. |
| 6,309,668 B1 | 10/2001 | Bastin et al. |
| 6,310,072 B1 | 10/2001 | Smith et al. |
| 6,328,979 B1 | 12/2001 | Yamashita et al. |
| 6,335,033 B2 | 1/2002 | Oshlack et al. |
| 6,375,957 B1 | 4/2002 | Kaiko et al. |
| 6,379,707 B2 | 4/2002 | Vladyka, Jr. et al. |
| 6,475,494 B2 | 11/2002 | Kaiko et al. |
| 6,692,767 B2 | 2/2004 | Burnside et al. |
| 6,696,088 B2 | 2/2004 | Oshlack et al. |
| 6,706,281 B2 | 3/2004 | Oshlack et al. |
| 6,723,343 B2 | 4/2004 | Kugelmann |
| 6,743,442 B2 | 6/2004 | Oshlack et al. |
| 6,919,372 B1 | 7/2005 | Yamashita et al. |
| 7,011,846 B2 | 3/2006 | Shojaei et al. |
| 7,261,529 B2 | 8/2007 | Persyn et al. |
| 7,399,488 B2 | 7/2008 | Hirsh et al. |
| 7,670,612 B2 | 3/2010 | Miller |
| 7,771,707 B2 | 8/2010 | Hirsh et al. |
| 8,449,909 B2 | 5/2013 | Hirsh et al. |
| 8,557,291 B2 | 10/2013 | Rariy et al. |
| 8,758,813 B2 | 6/2014 | Hirsh et al. |
| 8,840,928 B2 | 9/2014 | Rariy et al. |
| 9,044,398 B2 | 6/2015 | Hirsh et al. |
| 9,248,195 B2 | 2/2016 | Rariy et al. |
| 9,592,200 B2 | 3/2017 | Rariy et al. |
| 9,682,075 B2 | 6/2017 | Rariy et al. |
| 9,737,530 B1 | 8/2017 | Saim et al. |
| 9,763,883 B2 | 9/2017 | Hirsh et al. |
| 2001/0006650 A1 | 7/2001 | Burnside et al. |
| 2001/0036476 A1 | 11/2001 | Oshlack et al. |
| 2002/0032166 A1 | 3/2002 | Shefter et al. |
| 2002/0081333 A1 | 6/2002 | Oshlack et al. |
| 2003/0059397 A1 | 3/2003 | Hughes |
| 2003/0064099 A1 | 4/2003 | Oshlack et al. |
| 2004/0052731 A1 | 3/2004 | Hirsh et al. |
| 2004/0062778 A1 | 4/2004 | Shefer et al. |
| 2004/0170680 A1 | 9/2004 | Oshlack et al. |
| 2005/0013862 A1 | 1/2005 | Tobyn et al. |
| 2005/0181050 A1 | 8/2005 | Hirsh et al. |
| 2005/0281748 A1 | 12/2005 | Hirsh et al. |
| 2006/0104909 A1 | 5/2006 | Vaghefi et al. |
| 2006/0110457 A1 | 5/2006 | Labrecque et al. |
| 2007/0054002 A1 | 3/2007 | Persyn et al. |
| 2008/0199530 A1 | 8/2008 | Hirsh et al. |
| 2008/0260819 A1 | 10/2008 | Fleming et al. |
| 2009/0142378 A1 | 6/2009 | Frisbee |
| 2009/0297617 A1 | 12/2009 | Rariy et al. |
| 2010/0260834 A1 | 10/2010 | Hirsh et al. |
| 2011/0142943 A1 | 6/2011 | Rariy et al. |
| 2013/0045960 A1 | 2/2013 | Hirsh et al. |
| 2013/0310413 A1 | 11/2013 | Hirsh et al. |
| 2014/0105987 A1 | 4/2014 | Rariy et al. |
| 2014/0121232 A1 | 5/2014 | Hirsh et al. |
| 2015/0004244 A1 | 1/2015 | Rariy et al. |
| 2015/0005332 A1 | 1/2015 | Rariy et al. |
| 2015/0265596 A1 | 9/2015 | Hirsh et al. |
| 2016/0074326 A1 | 3/2016 | Rariy et al. |
| 2017/0182032 A1 | 6/2017 | Rariy et al. |
| 2017/0319575 A1 | 11/2017 | Rariy et al. |
| 2017/0360710 A1 | 12/2017 | Hirsh et al. |

FOREIGN PATENT DOCUMENTS

| | | |
|---|---|---|
| EP | 0253104 A1 | 1/1988 |
| EP | 0375063 A1 | 6/1990 |
| EP | 0578231 A1 | 1/1994 |
| EP | 0647448 A1 | 4/1995 |
| GB | 1513166 | 6/1978 |
| WO | WO 93/10765 A1 | 6/1993 |
| WO | WO 95/20947 A1 | 8/1995 |
| WO | WO 97/14438 A1 | 4/1997 |
| WO | WO 97/49402 A1 | 12/1997 |
| WO | WO 1998/002187 A1 | 1/1998 |
| WO | WO 98/18827 A1 | 5/1998 |
| WO | WO 1999/001111 A1 | 1/1999 |
| WO | WO 1999/042086 A1 | 8/1999 |
| WO | WO 00/50007 A1 | 8/2000 |
| WO | WO 01/08661 A2 | 2/2001 |
| WO | WO 01/58447 A1 | 8/2001 |
| WO | WO 01/72338 A1 | 10/2001 |
| WO | WO 2002/013786 A2 | 2/2002 |
| WO | WO 03/004029 A1 | 1/2003 |
| WO | WO 2004/004693 A1 | 1/2004 |
| WO | WO 2004/075877 A1 | 9/2004 |
| WO | WO 2005/123039 A1 | 12/2005 |

OTHER PUBLICATIONS

"International Preliminary Report on Patentability," 3 pages, PCT appl. No. PCT/US03/21095 (dated Apr. 25, 2005).

"International Preliminary Report on Patentability," 6 pages, PCT appl. No. PCT/US2005/020588 (dated Oct. 2, 2006).

"International Search Report," 2 pages, PCT appl. No. PCT/US03/21095 (dated Nov. 6, 2003).

"International Search Report," 4 pages, PCT appl. No. PCT/US2005/020588 (dated Sep. 9, 2005).

"International Search Report," 2 pages, PCT appl. No. PCT/US2016/050092 (dated Nov. 22, 2016).

(56) References Cited

OTHER PUBLICATIONS

"Supplementary European Search Report," 7 pages, EP appl. No. 03763229.6 (dated Sep. 19, 2008).
"Written Opinion of the International Searching Authority," 6 pages, PCT appl. No. PCT/US2005/020588 (dated Sep. 9, 2005).
"Written Opinion," 4 pages, PCT appl. No. PCT/US03/21095 (dated Jun. 20, 2004).
"Written Opinion of the International Searching Authority," 7 pages, PCT appl. No. PCT/US2016/050092 (dated Nov. 22, 2016).
Abuse and Mental Health Services Administration, "Results from the 2004 National Survey on Drug Use and Health: National Findings," pp. 1-310 (2005).
Buist et al., "Four salt phases of theophylline," Struct. Chem. Acta Crystal. Sect. C C70:220-224 (2014).
Bush et al., "A comparison of a theophylline-ephedrine combination with terbutaline," Ann. Allergy 41:13-17 (1978) abstract.
Chemical Abstract Society (CAS), Properties for HPMC (CAS reg. No. 9004-65-3) accessed Jun. 29, 2013.7 pages.
Choi et al., "Hydrophobic ion pair formation between leuprolide and sodium oleate for sustained release from biodegradable polymeric microspheres," Int. J. Pharm. 203:193-202 (2000).
Cortesi, et al., "Sugar cross-linked gelatin for controlled release: microspheres and disks," Biomaterials 19:1641-1649 (1998).
Gennaro, ed., Remington: The Science and Practice of Pharmacology, 20th ed., Lipincott: Baltimore, MD, pp. 704-706 (2000).
Lan et al., "Studies on the Synthesis and Thermal Properties of Copoly(L-lactic acid/glycolic acid) by Direct Melt Polycondensation," J. Appl. Polymer Sci. 92:2163-2168 (2004).
Nakamura, et al., "Development of an oral sustained release drug delivery system utilizing pH-dependent swelling of carboxyvinyl polymer", J. Control. Rel., 111:309-315 (2006).
Ozturk et al., "Mechanism of Release from Pellets Coated with an Ethylcellulose-Based Film," J. Control. Rel. 14:203-213 (1990).
Raffin et al., "Sodium pantoprazole-loaded enteric microparticles prepared by spray drying: Effect of the scale of production and process validation," Int. J. Pharm. 324:10-18 (2006).
Redden et al., "In vitro hydrolysis of polyunsaturated fatty acid N-acyloxymethyl derivatives of theophylline," Int. J. Pharm. 165:87-96 (1998).
Rodriguez et al., "Description and preliminary evaluation of a new ultrasonic atomizer for spray-congealing processes," Int. J. Pharm. 183(2):133-143 (1999).
Takka et al., "Effect of anionic polymers on the release of propanol hydrochloride from matrix tablets," Eur. J. Pharm. Biopharm. 52:75-82 (2001).
U.S. Appl. No. 14/320,086, "Tamper-Resistant Pharmaceutical Compositions of Opiods and Other Drugs," Rariy et al., 43 pages (filed Jun. 30, 2014).
U.S. Appl. No. 14/321,125, "Tamper-Resistant Pharmaceutical Compositions of Opiods and Other Drugs," Rariy et al., 43 pages (filed Jul. 1, 2014).
U.S. Department of Health and Human Services et al., "Abuse-Deterrent Opioids—Evaluation and Labeling. Guidance for Industry," http://www.fda.gov/Drugs/GuidanceComplianceRegulatoryInformation/Guidances/default.htm, 29 pages (Apr. 2015).
Yow et al., "Combined Streptomycin and Erythromycin Therapy in Subacute Bacterial Endocarditis," Am. J. Med. 16(4):613 (Apr. 1954).
Berkland, et al., "Fabrication of PLG microspheres with precisely controlled and monodisperse size distributions." Journal of Controlled Release (2001); 73(1): 59-74.
Choi, et al., "Effect of polymer molecular weight on nanocomminution of poorly soluble drug." Drug Delivery (2008); 15(5): 347-353.
Emås and Nyqvist, "Methods of studying aging and stabilization of spray-congealed solid dispersions with carnauba wax." International Journal of Pharmaceutics (2000); 197(1-2): 117-127, 13 pages.
Gandhi, et al., "Extrusion and spheronization in the development of oral controlled-release dosage forms." Pharmaceutical Science & Technology Today (1999); 2(4): 160-170.
Guidance for Industry Q1A(R2) Stability Testing of New Drug Substances and Products, U.S. Department of Health and Human Services Food and Drug Administration, Center for Drug Evaluation and Research (CDER), Center for Biologics Evaluation and Research (CBER) ("FDA Guidance"), Nov. 2003, ICH Revision 2, 25 pages.
Handbook of Pharmaceutical Excipients, 2nd ed., (eds. Wade and Weller), American Pharmaceutical Association (1994), pp. 82-83, 325-328, 544-545; 552-553; and 558-561, 16 pages.
Hawley's Condensed Chemical Dictionary, 13th ed., John, Wiley & Sons, Inc., New York, 1997, p. 1178, defining "wax", 4 pages.
Kim and Pack, Microspheres for Drug Delivery, in BioMEMS and Biomedical/Nanotechnology, pp. 19-50, Springer US (2006), 34 pages.
Leuner and Dressman, "Improving drug solubility for oral delivery using solid dispersions." European Journal of Pharmaceutics and Biopharmaceutics (2000); 50(1): 47-60.
Meyer and Manning, "Hydrophobic Ion Pairing: Altering the Solubility Properties of Biomolecules." Pharmaceutical Research (1998); 15(2): 188-193.
Murthy and Ghebre-Sellassie, "Current perspectives on the dissolution stability of solid oral dosage forms." Journal of Pharmaceutical Sciences (1993); 82(2): 113-126.
Pöyhia, et al., "The pharmacokinetics and metabolism of oxycodone after intramuscular and oral administration to healthy subjects." British Journal of Clinical Pharmacology (1992); 33(6): 617-621.
Sjökvist, et al., "Physicochemical aspects of drug release. XIV. The effects of some ionic and non-ionic surfactants on properties of a sparingly soluble drug in solid dispersions." International Journal of Pharmaceutics (1992); 79(1-3): 123-133.
Toxicological Evaluation of Some Food Colours, Emulsifiers, Stabilizers, Anti-Caking Agents and Certain Other Substances FAO Nutrition Meetings Report Series No. 46A WHO/FEED ADD/70. 36, Report on Deliberations of the Joint FAO/WHO Expert Committee on Food Additives, Rome, May 27-Jun. 4, 1969 ("FAO/WHO report"), 162 pages.
U.S. Appl. No. 10/614,866, filed Jul. 7, 2003, now U.S. Pat. No. 7,399,488 B2.
U.S. Appl. No. 12/473,073, filed May 27, 2009, now U.S. Pat. No. 8,557,291 B2.
U.S. Appl. No. 12/965,572, filed Dec. 10, 2010, now U.S. Pat. No. 8,840,928 B2.
U.S. Appl. No. 13/551,455, filed Jul. 17, 2012, now U.S. Pat. No. 9,044,398 B2.
U.S. Appl. No. 14/054,513, filed Oct. 15, 2013, now U.S. Pat. No. 9,248,195 B2.
U.S. Appl. No. 14/320,086, filed Jun. 30, 2014, now U.S. Pat. No. 9,682,075 B2.
U.S. Appl. No. 14/321,125, filed Jul. 1, 2014.
U.S. Appl. No. 14/717,232, filed May 20, 2015.
U.S. Appl. No. 14/946,275, filed Nov. 19, 2015, now U.S. Pat. No. 9,592,200 B2.
U.S. Appl. No. 15/457,153, filed Mar. 13, 2017.
U.S. Appl. No. 15/606,112, filed May 26, 2017.
U.S. Appl. No. 15/725,818, filed Oct. 5, 2017.
U.S. Appl. No. 15/727,134, filed Oct. 6, 2017.
U.S. Appl. No. 11/149,867, filed Jun. 10, 2005, now U.S. Pat. No. 7,771,707 B2.
U.S. Appl. No. 12/823,628, filed Jun. 25, 2010, now U.S. Pat. No. 8,449,909 B2.
U.S. Appl. No. 13/870,690, filed Apr. 25, 2013, now U.S. Pat. No. 8,758,813 B2.
U.S. Appl. No. 14/147,088, filed Jan. 3, 2014, now U.S. Pat. No. 9,763,883 B2.
U.S. Appl. No. 15/681,586, filed Aug. 21, 2017.
U.S. Appl. No. 15/255,859, filed Sep. 2, 2016, now U.S. Pat. No. 9,737,530 B1.

PROCESS OF MAKING STABLE ABUSE-DETERRENT ORAL FORMULATIONS

CROSS-REFERENCE TO RELATED APPLICATION

This application is a continuation of U.S. application Ser. No. 15/255,859, filed on Sep. 2, 2016, which claims the benefit of priority to U.S. Provisional Patent Application No. 62/353,839 filed Jun. 23, 2016, the disclosures of each of which are hereby incorporated by reference in their entirety for all purposes.

FIELD

The present disclosure is generally directed to the field of pharmaceutical compositions, such as compositions designed to reduce the potential for improper administration of drugs that are subject to abuse, extended-release compositions, methods of making such compositions with improved dissolution stability, and methods of using the same for treatment of pain.

BACKGROUND

Opioids such as oxycodone in the form of extended-release (ER) formulations are used to manage moderate to severe chronic pain. Although usually a safe and effective treatment option for patients with chronic pain who are appropriately managed and monitored, ER opioid formulations are associated with high rates of misuse, abuse, and diversion. This is in large part because oral ER opioids carry a large opioid load. Abusers often manipulate (e.g., cut, crush, or dissolve) ER formulations to more rapidly release most, if not all, of the active drug, with the goal of achieving a quick drug high. Further, misuse can occur when patients or their caregivers manipulate ER formulations for any number of reasons, including to reduce the dose or make the medication easier to swallow. Manipulation of most ER opioid formulations, regardless of intent, can result in greater exposure to drug than intended, which can lead to adverse consequences or even death. These challenges have led to the development of ER opioid formulations with properties intended to make product manipulation more difficult. Often referred to as abuse-deterrent, many of these formulations incorporate physical or chemical barriers to mechanical or chemical manipulations.

The DETERx® platform technology is an abuse-deterrent formulation strategy which consists of an active drug dissolved or dispersed in a melt comprising a hydrophobic fatty acid and a wax matrix (optionally including other excipients) that is then formed into particles, for example microspheres, e.g., using a spinning disk or other suitable atomizing or milling process. The microparticles (or microspheres, if produced by a process resulting in spherical particles), along with small quantities of external processing excipients are encapsulated into hard shell capsules or other suitable dosage forms. The microparticles are designed to preserve the extended release characteristics on physical manipulation by means such as crushing with household tools or by chewing. These properties are a consequence of the small size of the extended-release microparticles, along with the physiochemical properties of the inactive ingredients. Additionally, the fatty acid and active ingredient component of DETERx microspheres are selected such that they are associated via an ionic interaction (i.e., salt) in the solid microparticles. This interaction allows the active component to be dissolved during the melt formulation process, and allows for the formation of a solid solution. The creation of a solid solution of drug in hydrophobic materials further reduces the extractability and contributes to the abuse-deterrent properties of the formulation.

The microspheres in oxycodone DETERx are produced using a spray-congealing process from a hot melt. When using a spray congealing process, such as a spinning disk atomization process, the microspheres are formed nearly instantaneously as the melt is atomized. For pharmaceutical products, changes to the product during the normal product shelf-life at recommended storage conditions (i.e., room temperature) should be minimized to the extent possible. For this reason, pharmaceutical products are routinely tested by subjecting the product to stability studies in the commercial packaging configuration. Stability study requirements are outlined in US Food and Drug Administration (FDA) and International Conference on Harmonization (ICH) guidances, including ICH Q1A(R2), "Stability Testing of New Drug Substances and Products", November 2003. Product attributes tested during stability studies include, for example, tests for potency, purity, microbial attributes and drug release rate using standardized dissolution apparatus.

The present invention relates to a process for manufacturing extended-release microparticles with improved dissolution stability. The process of the present invention is related to microparticles comprising an active drug, one or more fatty acids and one or more wax components manufactured by congealing from a hot-melt process. It has been unexpectedly found that curing the product at one or more temperatures within the range from 25° C. up to an inversion temperature, for a minimum period of time, is required to effectively stabilize the dissolution profiles of such compositions. Curing outside this range will have either no significant effect or an adverse effect on product stability. The existence or identification of this inversion temperature and its role in curing has not previously been disclosed for such formulations.

The present inventors have developed a manufacturing process that utilizes curing within a specific temperature range to produce pharmaceutical compositions with improved dissolution stability. This process can be applied in making pharmaceutical formulations containing active drugs, such as opioids.

SUMMARY OF THE DISCLOSURE

This disclosure provides a process of making abuse-deterrent pharmaceutical formulations. In one embodiment, the process requires forming an abuse-deterrent formulation and then curing the composition. In one embodiment, the process of making an abuse-deterrent formulation comprises the steps of: preparing a mixture comprising (i) one or more pharmaceutically acceptable waxes, one or more drugs, and one or more pharmaceutically acceptable fatty acids, or (ii) one or more drugs in the form of a fatty acid salt, one or more pharmaceutically acceptable waxes, at a temperature sufficient to form a substantially homogeneous melt; b) forming solid microparticles from the substantially homogeneous melt; c) optionally further formulating the solid microparticles with additional pharmaceutically acceptable excipients, and d) curing the solid microparticles or formulated microparticles at one or more temperatures within the range of 25° C. up to and including the inversion temperature, for a minimum of about 48 hours.

In one embodiment of the disclosed process, the cured microparticles or cured formulated microparticles exhibit less change in the dissolution profile after storing for 6 months at 25° C. and 60% relative humidity (RH) than otherwise identical uncured formulated microparticles after storing for 6 months at 25° C. and 60% RH when dissolution is conducted at 100 RPM using USP Apparatus I in 900 mL of pH 4.5 sodium acetate buffer supplemented with 0.03% Tween 20 at 37° C.

In one embodiment of the disclosed process, the cured microparticles or cured formulated microparticles exhibit less than a 15% change in the mean percent drug released at the 4 hour dissolution time point after storage for 6 months at 25° C. and 60% RH. In another embodiment, the cured microparticles or cured formulated microparticles exhibit less than a 10% change in the mean percent drug released at the 4 hour dissolution time point after storage for 6 months at 25° C. and 60% RH. In another embodiment, the cured microparticles or cured formulated microparticles exhibit less than a 5% change in the mean percent drug released at the 4 hour dissolution time point after storage for 6 months at 25° C. and 60% RH. In other embodiments, the cured microparticles or cured formulated microparticles exhibit less than a 2.5% change in the mean percent drug released at the 4 hour dissolution time point after storage for 6 months at 25° C. and 60% RH.

In one embodiment of the disclosed process, the fatty acid is myristic acid, the drug is oxycodone, and the inversion temperature is approximately 36° C.

In another embodiment of the disclosed process, the fatty acid is stearic acid, the drug is oxycodone, and the inversion temperature is approximately 53° C.

In one embodiment of the disclosed process, the microparticles are cured at a first temperature above the inversion temperature and subsequently a second temperature below the inversion temperature.

In one embodiment, the present disclosure provides a pharmaceutical composition prepared by the process comprising the steps of: a) mixing one or more drugs, one or more pharmaceutically acceptable waxes, and one or more pharmaceutically acceptable fatty acids at a temperature sufficient to form a substantially homogeneous melt; b) forming solid microparticles from the substantially homogeneous melt; c) optionally further formulating the solid microparticles with additional pharmaceutically acceptable excipients, and d) curing the solid microparticles or formulated microparticles at one or more temperatures within the range of 25° C. up to and including the inversion temperature, for a minimum of about 48 hours. In another embodiment, the present disclosure provides a pharmaceutical composition prepared by the process comprising the steps of: a) mixing one or more fatty acid salts of one or more drugs, one or more pharmaceutically acceptable waxes, at a temperature sufficient to form a substantially homogeneous melt; b) forming solid microparticles from the substantially homogeneous melt; c) optionally further formulating the solid microparticles with additional pharmaceutically acceptable excipients, and d) curing the solid microparticles or formulated microparticles at one or more temperatures within the range of 25° C. up to and including the inversion temperature, for a minimum of about 48 hours. In another embodiment, a pharmaceutical composition comprises a composition prepared by any of the processes described herein, for example wherein the fatty acid is myristic acid, the drug is oxycodone, and the inversion temperature is approximately 36° C.

In another embodiment of the present disclosure, a capsule is provided comprising any one of the pharmaceutical compositions as described herein.

This disclosure provides a pharmaceutical formulation with improved dissolution stability. In one embodiment, the pharmaceutical formulation is a cured composition. In some embodiments, the cured composition is in a form of solid microparticles or formulated microparticles. In one embodiment, the pharmaceutically acceptable solid microparticles or formulated microparticles cured at one or more temperatures within the range of 25° C. up to and including the inversion temperature, for a minimum of about 48 hours comprise: a mixture of one or more drugs, one or more waxes, and a sufficient amount of one or more fatty acids to provide said mixture in substantially homogenous form during the melt manufacture of the microparticles.

In one embodiment of the disclosed microparticles, the fatty acid is myristic acid, and the drug is oxycodone.

This disclosure provides a method of treating pain comprising administering any one of the pharmaceutical compositions as described herein. In some embodiments of the methods disclosed herein, the pharmaceutical composition is prepared by the process comprising the steps of: a) preparing a mixture comprising (i) one or more drugs, one or more pharmaceutically acceptable waxes, and one or more pharmaceutically acceptable fatty acids, or (ii) one or more drugs in the form of a fatty acid salt and one or more pharmaceutically acceptable waxes at a temperature sufficient to form a substantially homogeneous melt; b) forming solid microparticles from the substantially homogeneous melt; c) optionally further formulating the solid microparticles with additional pharmaceutically acceptable excipients, and d) curing the solid microparticles or formulated microparticles at one or more temperatures within the range of 25° C. up to and including the inversion temperature, for a minimum of about 48 hours; wherein the fatty acid is myristic acid, the drug is oxycodone, and the inversion temperature is approximately 36° C.

In another embodiment of the method disclosed herein, a capsule comprising any one of the pharmaceutical compositions as disclosed herein is provided.

In another embodiment of the present disclosure, the method of treating pain is provided, wherein pharmaceutically acceptable solid microparticles or formulated microparticles cured at one or more temperatures within the range of 25° C. up to and including the inversion temperature, for a minimum of about 48 hours, as described herein, e.g. comprising: a mixture of one or more drugs, one or more waxes, and a sufficient amount of one or more fatty acids to provide said mixture in substantially homogenous form during the melt manufacture of the microparticles, is administered to a patient in need thereof. In one embodiment, the method of treating pain as disclosed herein comprises administering a pharmaceutically acceptable microparticles or formulated microparticles comprising myristic acid and oxycodone.

DETAILED DESCRIPTION OF THE FIGURES

FIG. 1. shows dissolution of capsules produced with uncured oxycodone containing microspheres after storage at 25° C./60% RH, 30° C./65% RH, and 40° C./75% RH for 3 months.

Figure 2A:
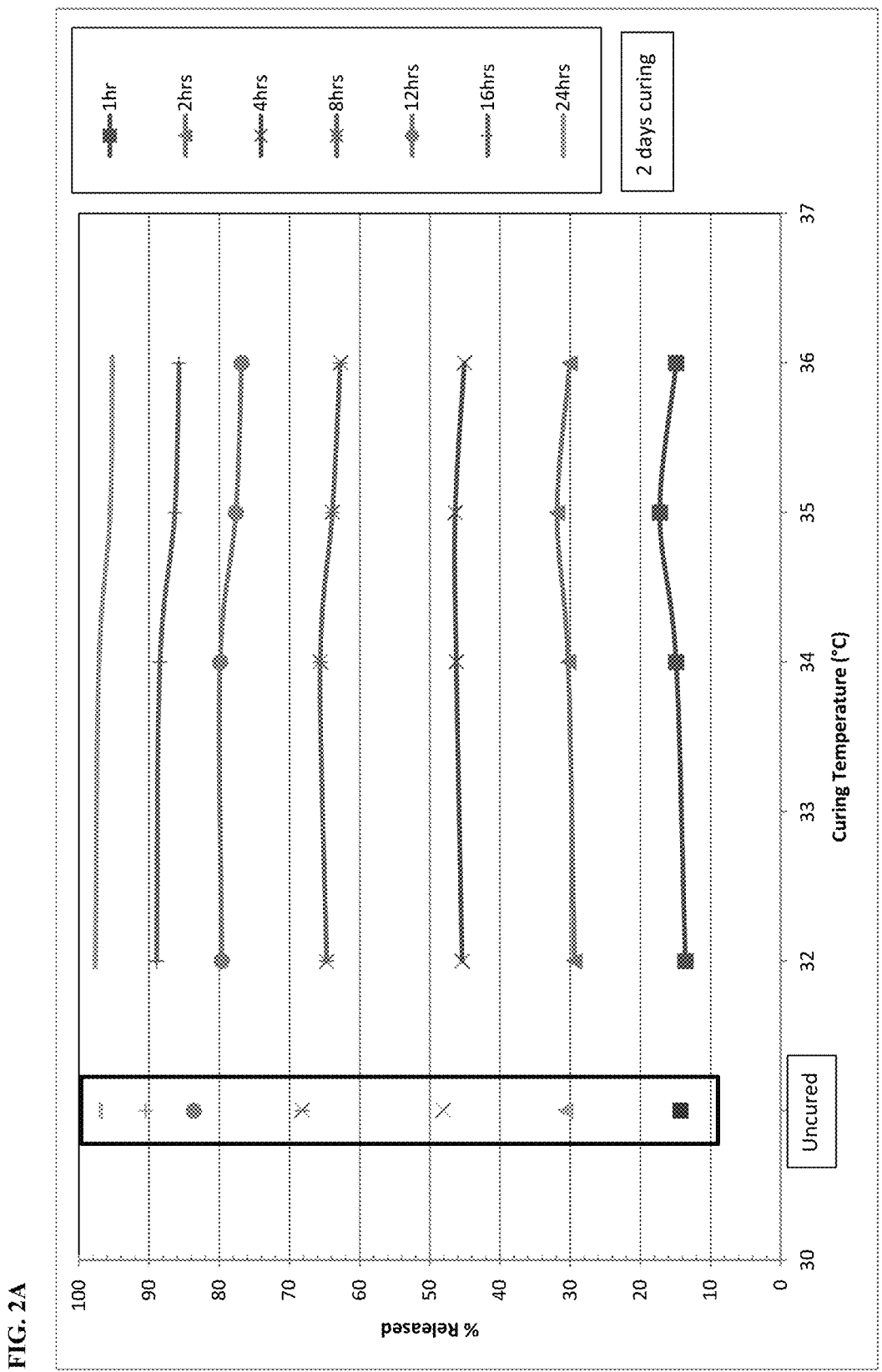

FIG. 2A. shows dissolution of capsules produced with oxycodone containing microspheres after single-stage curing between 32-36° C. for 2 days.

Figure 2B:
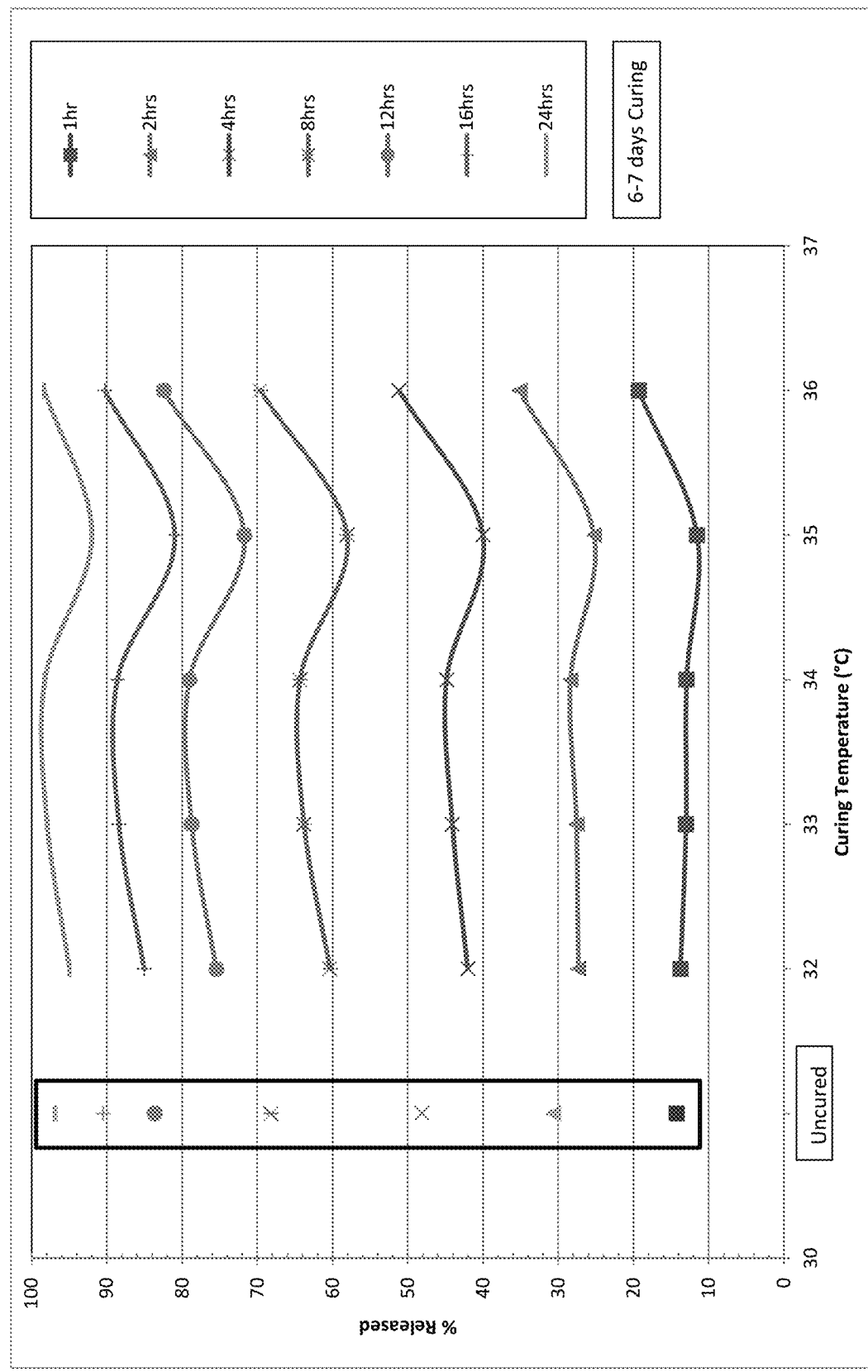

FIG. 2B. shows dissolution of capsules produced with oxycodone containing microspheres after single-stage curing between 32-36° C. for 6-7 days.

Figure 3A:
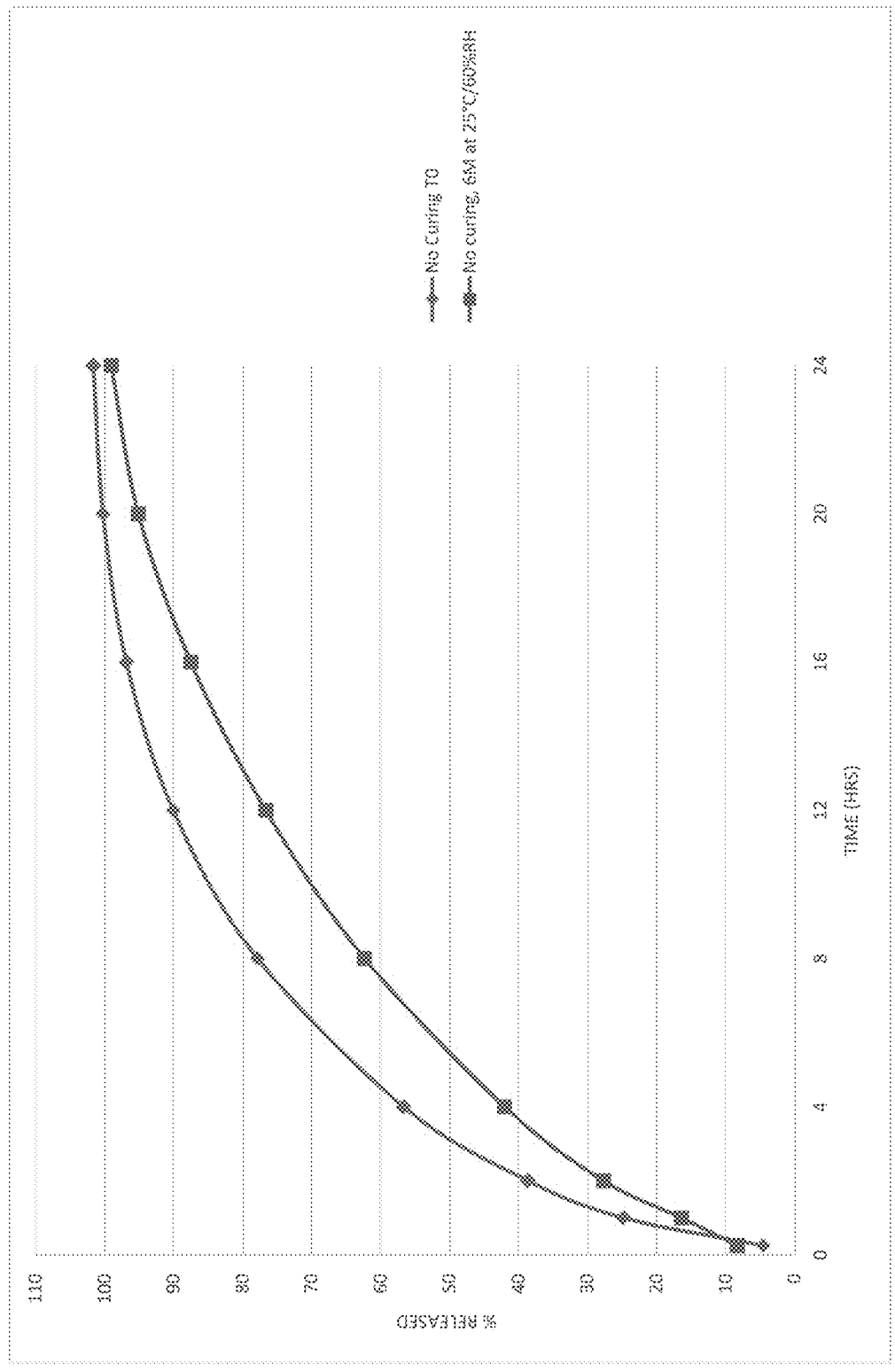

FIG. 3A. compares initial (T0) dissolution of a formulation of uncured oxycodone containing microspheres with dissolution of the same uncured formulation after 6 months of storage at 25° C./60% RH.

Figure 3B:
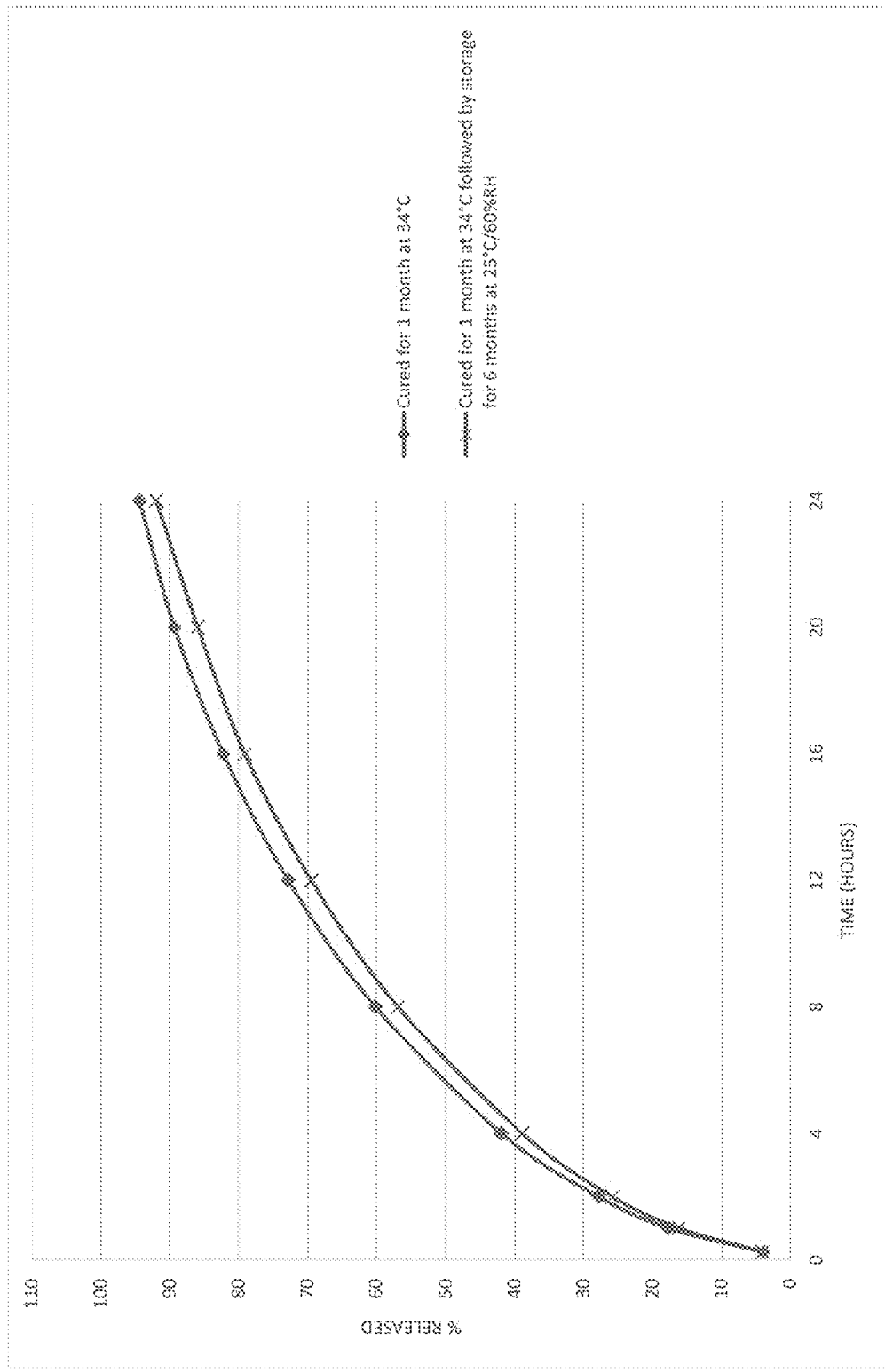

FIG. 3B. compares initial (T0) dissolution of a formulation of oxycodone containing microspheres cured in a single stage at 34° C. for 1 month with dissolution of the same cured formulation after 6 months of storage at 25° C./60% RH.

Figure 3C:
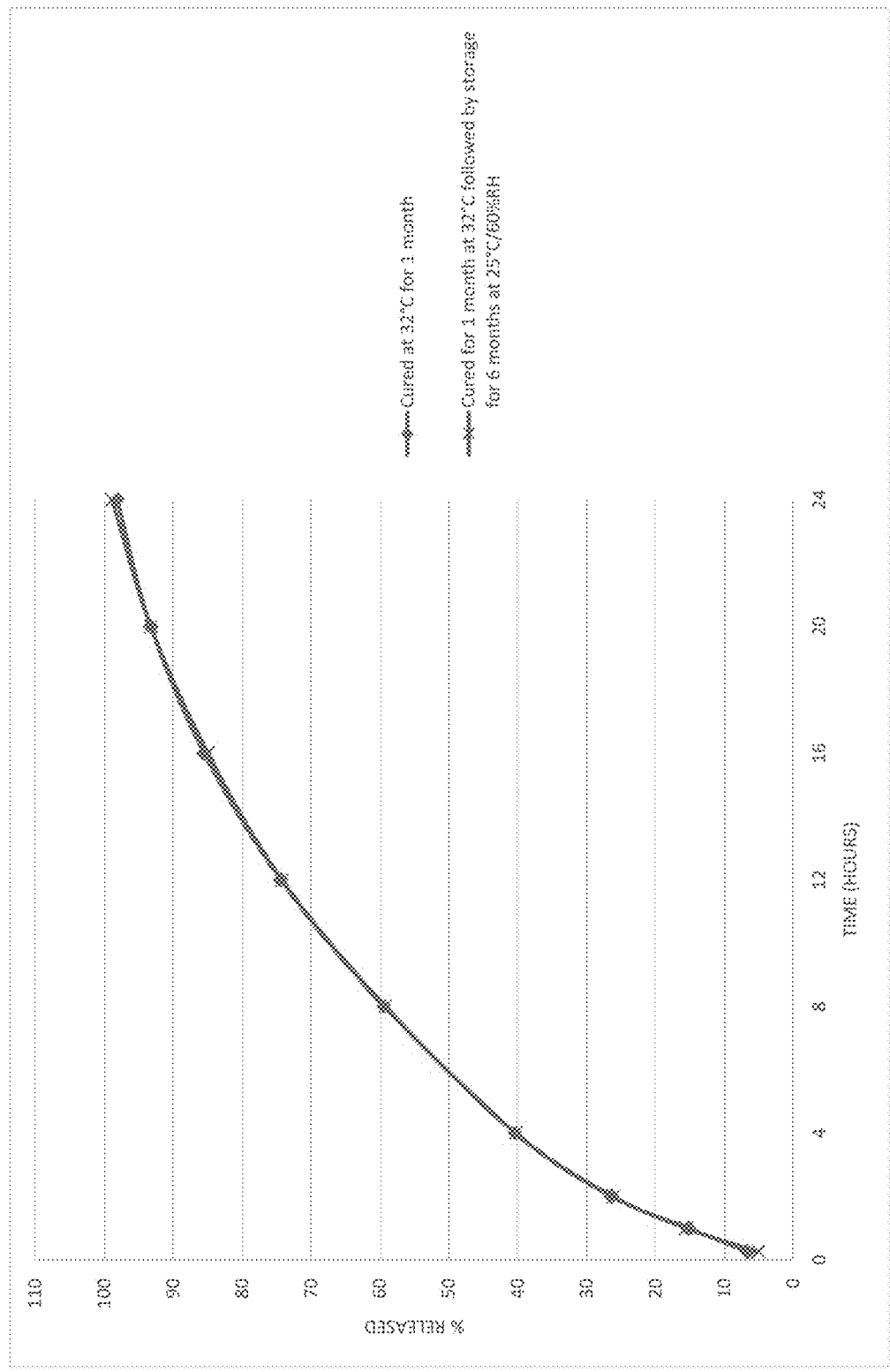

FIG. 3C. compares initial (T0) dissolution of a formulation of oxycodone containing microspheres cured in a single stage at 32° C. for 1 month with dissolution of the same cured formulation after 6 months of storage at 25° C./60% RH.

Figure 3D:
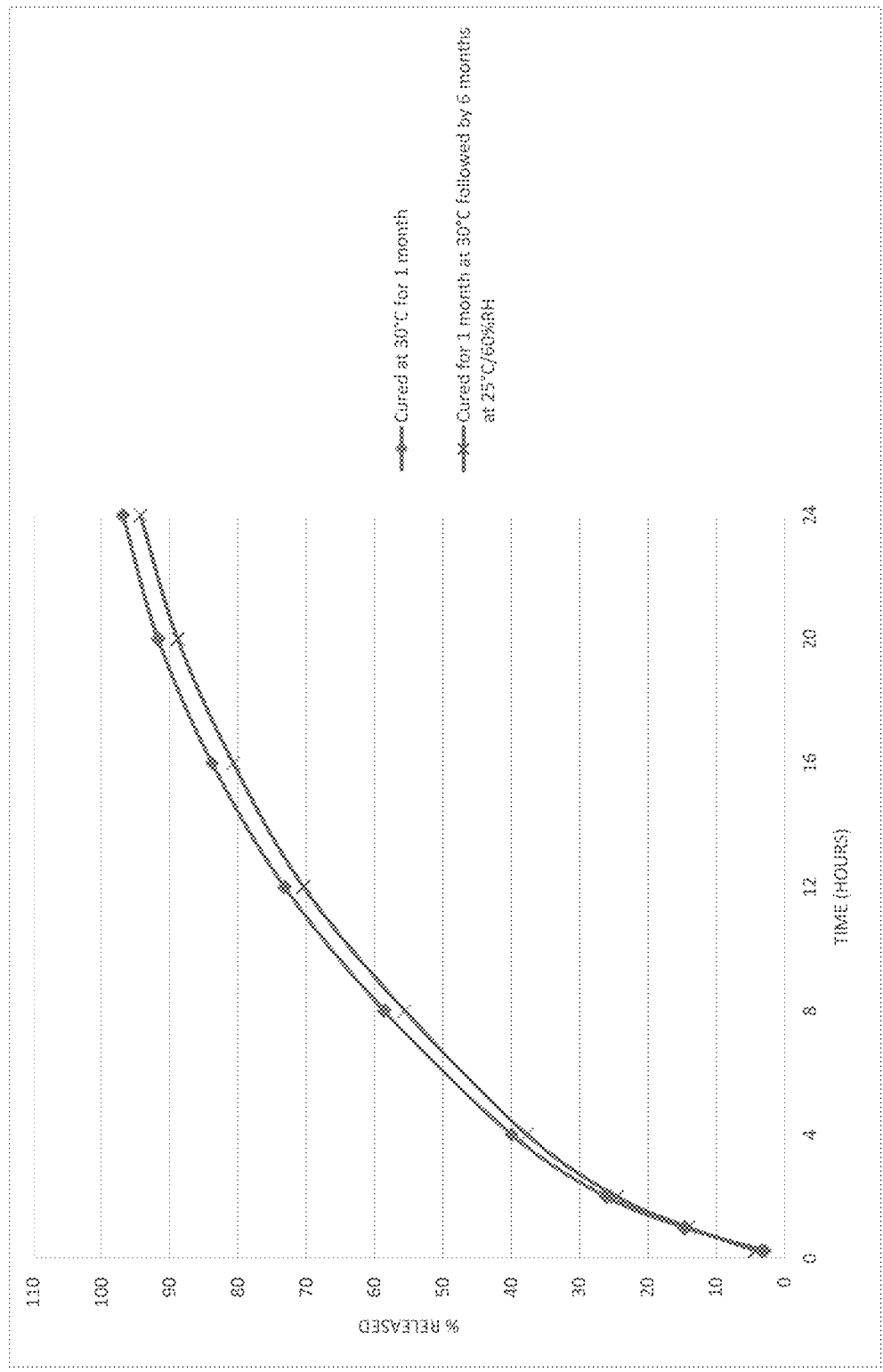

FIG. 3D. compares initial (T0) dissolution of a formulation of oxycodone containing microspheres cured in a single stage at 30° C. for 1 month with dissolution of the same cured formulation after 6 months of storage at 25° C./60% RH.

Figure 3E:
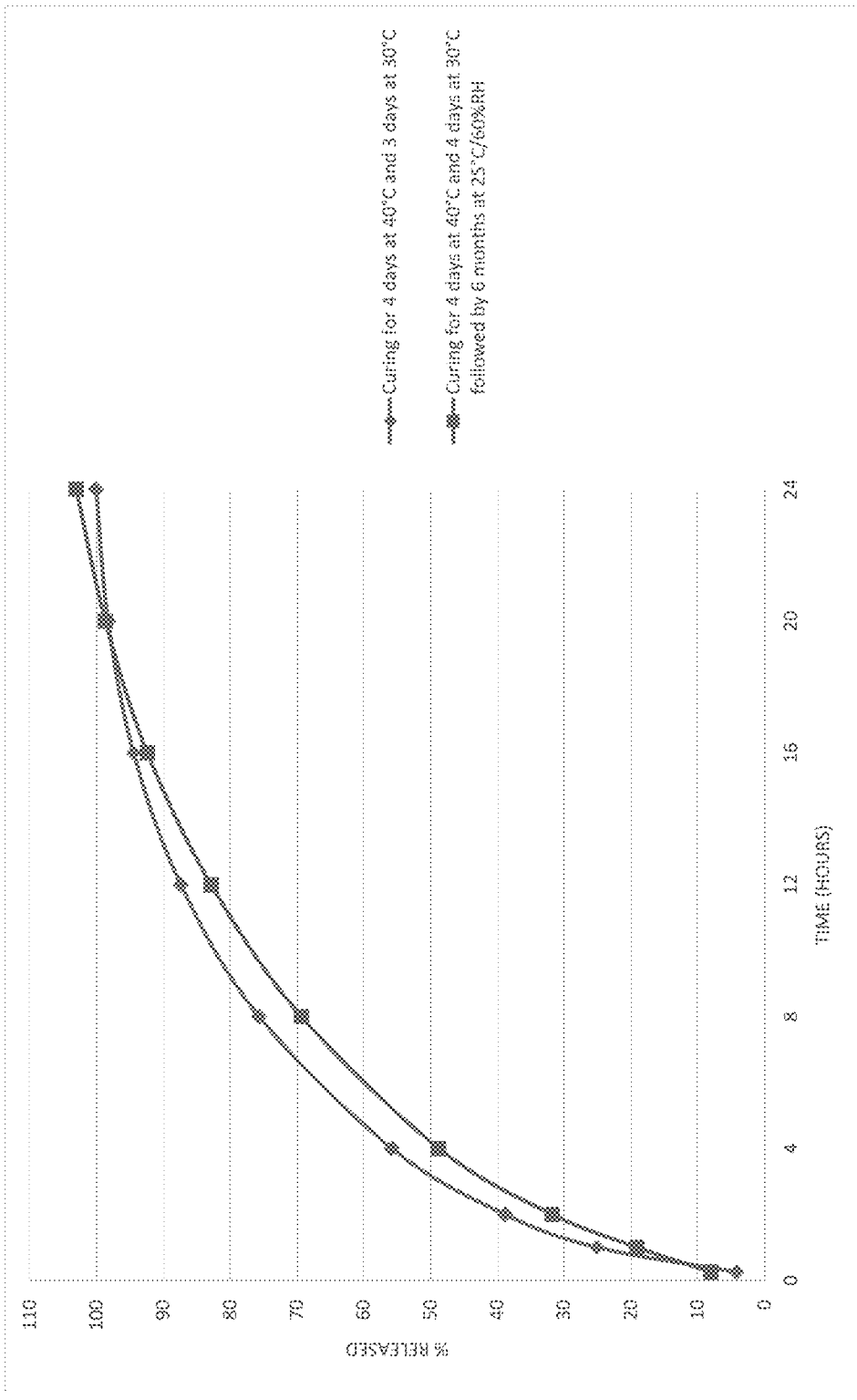

FIG. 3E. compares initial (T0) dissolution of a formulation of oxycodone containing microspheres cured in a 2-stage process (40° C./4d:30° C./3d) with dissolution of the same cured formulation after 6 months of storage at 25° C./60% RH.

Figure 4A:
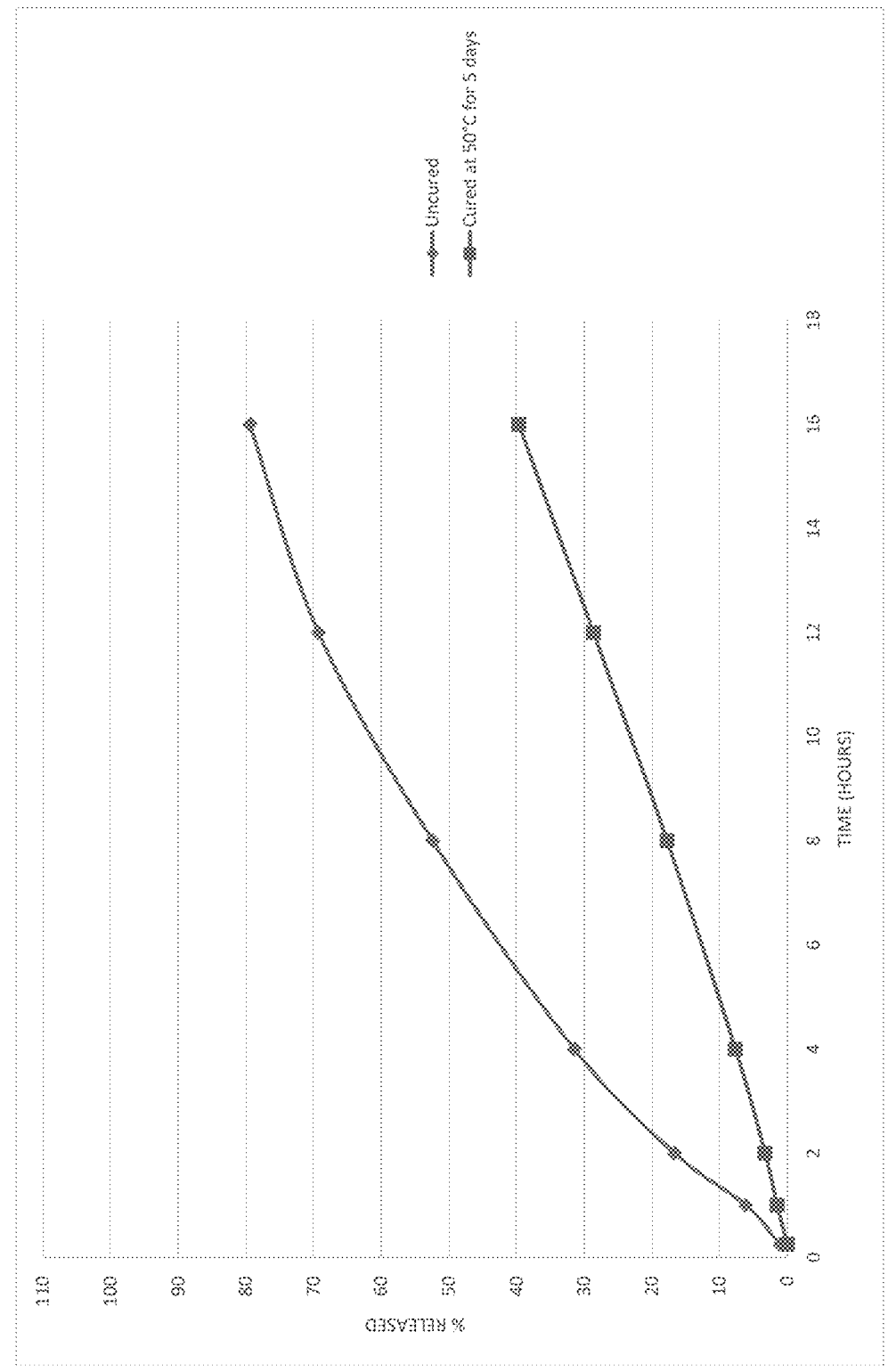

FIG. 4A. shows the dissolution behavior of a formulation of microspheres containing oxycodone and stearic acid after single stage curing at 50° C.

Figure 4B:
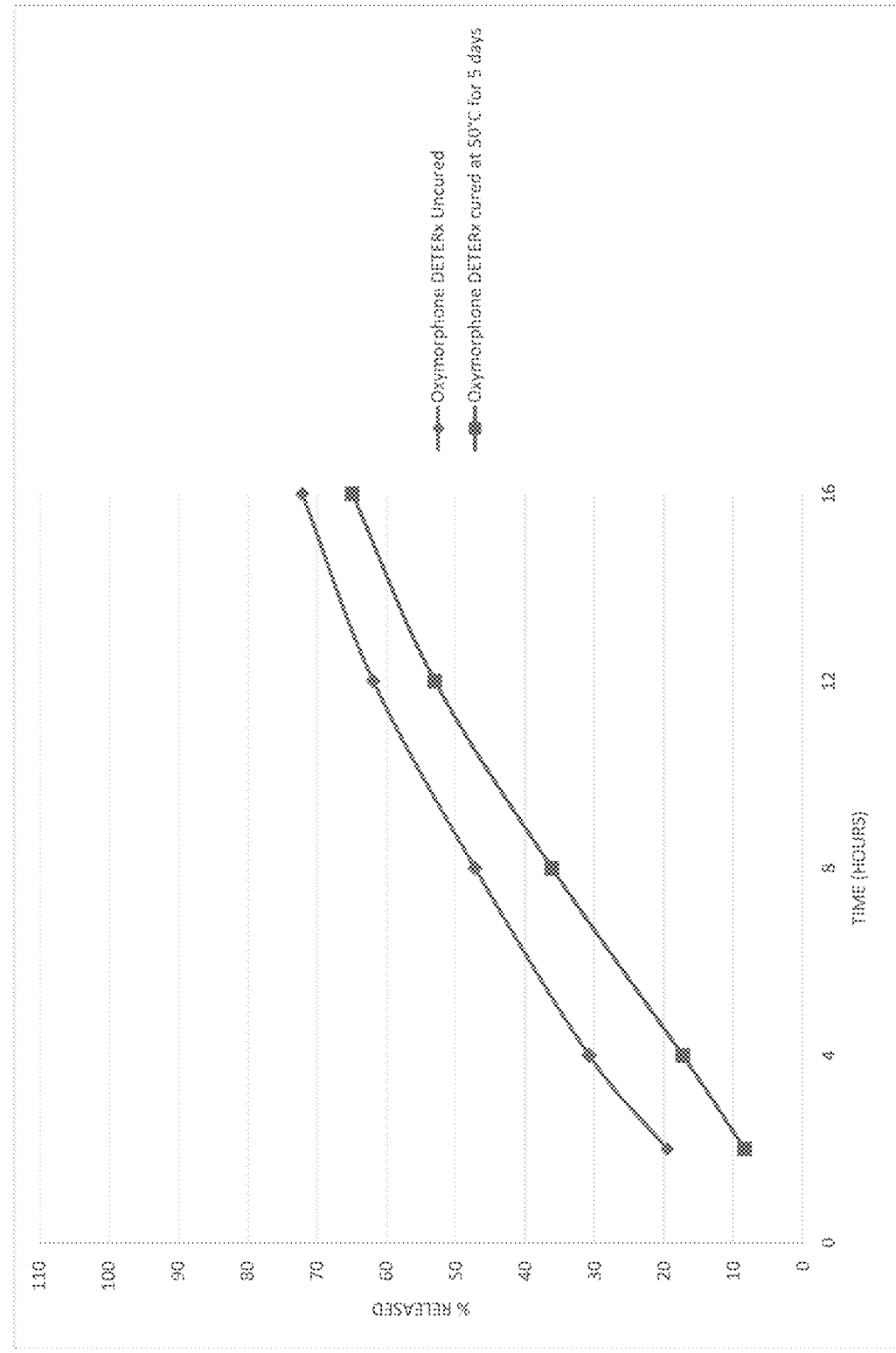

FIG. 4B. shows the dissolution behavior of a formulation of microspheres containing oxymorphone and stearic acid after single stage curing at 50° C.

Figure 4C:
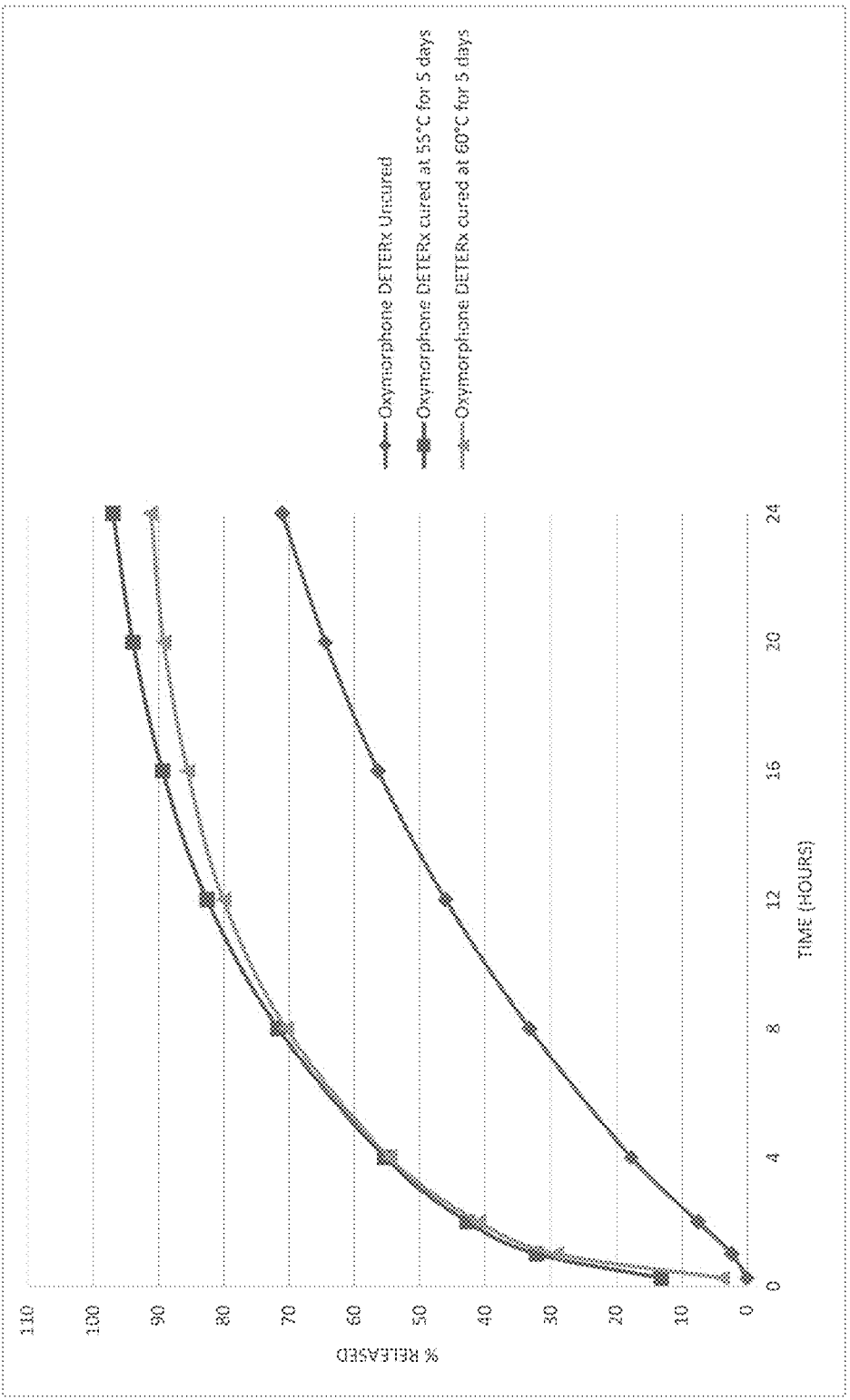

FIG. 4C. shows the dissolution behavior of formulation of microspheres containing oxymorphone and stearic acid after single stage curing at 55° C. and 60° C.

DETAILED DESCRIPTION OF THE DISCLOSURE

Definitions

While the following terms are believed to be well understood by one of ordinary skill in the art, the following definitions are set forth to facilitate explanation of the presently disclosed subject matter.

The term "a" or "an" refers to one or more of that entity; for example, "a halogen" refers to one or more halogens or at least one halogen. As such, the terms "a" (or "an"), "one or more" and "at least one" are used interchangeably herein. In addition, reference to "an alkyl group" by the indefinite article "a" or "an" does not exclude the possibility that more than one of the alkyl group is present, unless the context clearly requires that there is one and only one of the alkyl groups.

As used herein, the verb "comprise" as is used in this description and in the claims and its conjugations are used in its non-limiting sense to mean that items following the word are included, but items not specifically mentioned are not excluded.

As used herein, "curing" or "annealing" refers to a process used to stabilize excipients, intermediates and finished products over shorter time frames than would otherwise be realized at room temperature, for example by heating or maintaining under specified temperature, time, and, optionally, RH conditions.

As used herein, "formulated" (in the context of "formulated" microparticles) refers to microparticles (cured or uncured) combined with other excipients and/or further processed by means such as, but not limited to, tableting by compression or encapsulation.

As used herein "inversion temperature" is the temperature at or below which a composition of the present invention is cured to result in improved dissolution stability as described herein. The inversion temperature of a particular composition of the present invention can be determined empirically, e.g., as described in Example 2 herein.

The fatty acid salt is formed by interaction between the one or more fatty acids and one or more drugs wherein the fatty acid is present in excess of or below the concentration required for complete solubilization of the drugs in the melt. The fatty acid salt is dispersed within a wax composition and, optionally, other excipients in a solid, dissolved or melted state. As used herein, "substantially homogenous" with respect to the molten compositions or microparticles of the present disclosure refers specifically to the homogeneity of the fatty acid salt(s) of the one or more drugs in the waxy excipients. A substantially homogeneous combination of the fatty acid salt(s) of the one or more drugs and one or pharmaceutically acceptable waxes and other excipients means at least 50 mole % of the drug is homogeneously dissolved or dispersed in the wax composition. In other embodiments, the mole % of fatty acid salt of the drug dissolved or dispersed in the wax is at least 55%, 60%, 65%, 70%, 75%, 80%, 85%, 90%, 95%, 97%, 99%, or about 100%

As used herein, a "wax" or a "wax-like material" is defined as any pharmaceutically acceptable material, including any of a diverse class of organic compounds that are hydrophobic, malleable solids near ambient temperatures. They include higher alkanes and lipids, typically with melting points above about 40° C. (104° F.), melting to give low viscosity liquids. Waxes are virtually insoluble in water. Natural waxes of different types are produced by plants and animals and occur in petroleum and include those waxes disclosed herein.

As used herein, the symbol "≤" means "not more than" or "equal to or less than"; "<" means "less than"; "≥" means "not less than" or "equal to or more than"; and ">" means "more than". Furthermore, the numerical numbers, when used herein in connection with purity or impurity content, include not only the exact number but also the approximate range around the number. For example, the phrase "purity of 99.0%" denotes a purity of about 99.0%.

Pharmaceutical Compositions

The present disclosure provides a pharmaceutical composition designed to reduce the potential for improper administration of drugs that are subject to abuse. In one embodiment, the composition is in the form of or comprises microparticles formed from a melt manufacturing process. In another embodiment, the composition or a component of the composition is cured. In another embodiment, the composition of the present disclosure provides improved dissolution stability.

In one embodiment, a pharmaceutical composition of the present disclosure is or comprises solid microparticles. In one embodiment, pharmaceutically acceptable solid microparticles or formulated microparticles cured at a temperature within the range of 25° C. up to and including the inversion temperature, for a minimum of about 48 hours comprise: a mixture of one or more drugs, one or more waxes, and a sufficient amount of one or more fatty acids to provide said mixture in substantially homogenous form during the melt manufacture of the microparticles.

In one embodiment, one or more drugs are selected from Schedule II, III, IV or V drugs. In another embodiment, the one or more drugs are opioid analgesics.

In one embodiment, one or more drugs are selected from 1-phenylcyclohexylamine, 1-piperidinocyclohexanecarbonitrile, alfentanil, alphacetylmethadol, alphaprodine, alprazolam, amobarbital, amphetamine, anileridine, apomorphine, aprobarbital, barbital, barbituric acid derivatives, bemidone, benzoylecgonine, benzphetamine, betacetylmethadol, betaprodine, bezitramide, bromazepam, buprenorphine, butabarbital, butalbital, butorphanol, camazepam, cathine, chloral, chlordiazepoxide, clobazam, clonazepam, clorazepate, clotiazepam, cloxazolam, cocaine, codeine, chlorphentermine, delorazepam, dexfenfluramine, dextromoramide, dextropropoxyphen, dezocine, diazepam, diethylpropion, difenoxin, dihydrocodeine, dihydromorphine, dioxaphentyl butyrate, dipanone, diphenoxylate, diprenorphine, ecgonine, enadoline, eptazocine, estazolam, ethoheptazine, ethyl loflazepate, ethylmorphine, etorphine, femproponex, fencamfamin, fenfluramine, fentanyl, fludiazepam, flunitrazepam, flurazepam, glutethimide, halazepam, haloxazolam, hexalgon, hydrocodone, hydromorphone, isomethadone, hydrocodone, ketamine, ketazolam, ketobemidone, levanone, levoalphacetylmethadol, levomethadone, levomethadyl acetate, levomethorphan, levorphanol, lofentanil, loperamide, loprazolam, lorazepam, lormetazepam, lysergic acid, lysergic acid amide, mazindol, medazepam, mefenorex, mepetidine, meptazinol, metazocine, methadone, methamphetamine, methohexital, methotrimeprazine, methyl dihydromorphinone, methylphenidate, methylphenobarbital, metopon, morphine, nabilone, nalbuphine, nalbupine, nalorphine, narceine, nefopam, nicomorphine, nimetazepam, nitrazepam, nordiazepam, normethadone, normorphine, oxazepam, oxazolam, oxycodone, oxymorphone, pentazocine, pentobarbital. phenadoxone, phenazocine, phencyclidine, phendimetrazine, phenmetrazine, phenetidine, piminodine, prodilidine, properidine, propoxyphene, racemethorphan, racemorphan, racemoramide, remifentanil, secobarbital, sufentanil, talbutal, thebaine, thiamylal, thiopental, tramadol, trimeperidine, or vinbarbital, or a pharmaceutically acceptable salt or a stereoisomer thereof.

In addition, in one embodiment, the following scheduled drugs may be incorporated into the composition: allobarbitone, alprazolam, amylobarbitone, aprobarbital, barbital, barbitone, benzphetamine, brallobarbital, bromazepam, brotizolam, buspirone, butalbital, butobarbitone, bntorphanol, camazepam, captodiame, carbromal, carfentanil, carpipramine, cathine, chloral, chloral betaine, chloral hydrate, chloralose, chlordiazepoxide, chlorhexadol, chlormethiazole edisylate, chlormezanone, cinolazepam, clobazam, potassium clorazepate, clotiazepam, cloxazolam, cyclobarbitone, delorazepam, dexfenfluramine, diazepam, diethylpropion, difebarbamate, difenoxin, enciprazine, estazolam, ethyl loflazepate, etizolam, febarbamate, fencamfamin, fenfluramine, fenproporex, fluanisone, fludiazepam, flunitraam, flunitrazepam, flurazepam, flutoprazepam, gepirone, glutethimide, halazepam, haloxazolam, hexobarbitone, ibomal, ipsapirone, ketazolam, loprazolam mesylatc, lorazepam, lormetazepam, mazindol, mebutamate, medazepam, mefenorex, mephobarbital, meprobamate, metaclazepam, methaqualone, methohexital, methylpentynol, methylphenobarbital, midazolam, milazolam, morphine, nimetazepam, nitrazepam, nordiazepam, oxazepam, oxazolam, paraldehyde, pemoline, pentabarbitone, pentazocine, pentobarbital, phencyclidine, phenobarbital, phendimetrazine, phenmetrazine, phenprobamate, phentermine, phenyacetone, pinazepam, pipradol, prazepam, proxibarbal, quazepam, quinalbaritone, secobarbital, secbutobarbitone, sibutramine, temazepam, tetrazepam, triazolam, triclofos, zalepan, zaleplon, zolazepam, zolpidem, or zopiclone, or a pharmaceutically acceptable salt or a stereoisomer thereof.

The composition disclosed herein contemplates all such compounds, including cis- and trans-isomers, R- and S-enantiomers, diastereomers, (D)-isomers, (L)-isomers, the racemic mixtures thereof, compounds of different spacial conformations, and other mixtures thereof, as falling within the scope of the invention. Additional asymmetric carbon atoms may be present in a substituent such as an alkyl group. All such isomers, as well as mixtures thereof, are intended to be included in this disclosure.

In one embodiment, the one or more drugs is oxycodone or pharmaceutically acceptable salt thereof. In another embodiment, the one or more drugs is oxycodone hydrochloride. In a further embodiment the one or more drugs is a fatty acid salt of oxycodone. Suitable fatty acids include any of the fatty acids disclosed herein.

In one embodiment, the one or more drugs are provided in about 1 wt. % to about 60 wt. % of the pharmaceutical composition or the pharmaceutical microparticles. In another embodiment, the one or more drugs are provided in about 1 wt. % to about 20 wt. % or in about 1 wt. % to about 10 wt. % of the pharmaceutical composition or the pharmaceutical microparticles. In one embodiment, the one or more drugs are provided in about 1, about 2, about 3, about 4, about 5, about 6, about 7, about 8, about 9, about 10, about 11, about 12, about 13, about 14, about 15, about 16, about 17, about 18, about 19, or about 20 wt. % of the pharmaceutical composition or the pharmaceutical microparticles.

In one embodiment, the one or more drugs in a dosage form comprising any one of the compositions disclosed herein contains about 1 to about 100 mg of the drug. In one embodiment, the drug in a dosage form is about 5, 7.5, 10, 15, 20, 25, 30, 35, 40, 45, 50, 55, 60, 65, 70, 75, or 80 mg. In one embodiment, the dosage form comprises oxycodone or pharmaceutically acceptable salts thereof in amounts equivalent to about 9, 13.5, 18, 27, 36, 54, or 72 mg oxycodone base. When the drug is in the form of a salt, the weight percentage of drug salt in the compositions of the present invention is expressed as the equivalent weight of the non-salt (or free-base) form of the drug unless otherwise specified.

In one embodiment, the one or more waxes are selected from wax-like materials including natural or synthetic waxes, hydrocarbons, or normal waxes. Examples of waxes include, but are not limited to, beeswax, glycowax, castor wax, carnauba wax, paraffins and candelilla wax. In one embodiment, the one or more waxes are selected from carnauba wax, beeswax, and combinations thereof.

In one embodiment, the one or more waxes are provided in about 1 wt. % to about 80 wt. % of the pharmaceutical composition or the pharmaceutical microspheres. In another embodiment, the one or more waxes are provided in about 20 wt. % to about 80 wt. % or 30 wt. % to about 50 wt. % of the pharmaceutical composition or the pharmaceutical microparticles. In one embodiment, the one or more waxes are provided in about 10, about 11, about 12, about 13, about 14, about 15, about 16, about 17, about 18, about 19, about 20, about 21, about 22, about 23, about 24, about 25, about 26, about 27, about 28, about 29, about 30, about 31, about 32, about 33, about 34, about 35, about 36, about 37, about 38, about 39, about 40, about 41, about 42, about 43, about 44, about 45, about 46, about 47, about 48, about 49, about 50, about 51, about 52, about 53, about 54, about 55, about 56, about 57, about 58, about 59, or about 60, about 61, about 62, about 63, about 64, about 65, about 66, about 67, about 68, about 69, about 70, wt. % of the pharmaceutical composition or the pharmaceutical microparticles.

In one embodiment, the one or more fatty acids are selected from free fatty acids. In one embodiment, the one or more fatty acids are selected from lauric acid, myristic acid, stearic acid, or palmitic acid, or combinations thereof. In some embodiments, the one or more fatty acids are selected from substituted or unsubstituted C12-C40 fatty acids. In other embodiments, the one or more fatty acids are selected from substituted or unsubstituted C12-C20 fatty acids. In one embodiment, the one or more fatty acid is myristic acid. In other embodiments, the one or more fatty acid is stearic acid. In other embodiments, the one or more fatty acids is palmitic acid. In other embodiments the one or more fatty acids are a combination of palmitic and stearic acids.

In one embodiment, the one or more fatty acids are provided in an amount of about 1 wt. % to about 80 wt. % of the pharmaceutical composition or the pharmaceutical microspheres. In another embodiment, the one or more fatty acids are provided in an amount of about 20 wt. % to about 80 wt. % or 40 wt. % to about 60 wt. % of the pharmaceutical composition or the pharmaceutical microparticles. In one embodiment, the one or more fatty acids are provided in an amount of about 10, about 11, about 12, about 13, about 14, about 15, about 16, about 17, about 18, about 19, about 20, about 21, about 22, about 23, about 24, about 25, about 26, about 27, about 28, about 29, about 30, about 31, about 32, about 33, about 34, about 35, about 36, about 37, about 38, about 39, about 40, about 41, about 42, about 43, about 44, about 45, about 46, about 47, about 48, about 49, about 50, about 51, about 52, about 53, about 54, about 55, about 56, about 57, about 58, about 59, or about 60, about 61, about 62, about 63, about 64, about 65, about 66, about 67, about 68, about 69, or about 70, wt. % of the pharmaceutical composition or the pharmaceutical microparticles.

In one embodiment, the amount of one or more fatty acids sufficient to provide said mixture in substantially homogenous form during melt manufacture is determined by experimentation. In another embodiment, the amount of one or more fatty acids sufficient to provide said mixture in substantially homogenous form is about 40 wt. % to about 60 wt. % of the pharmaceutical composition or the pharmaceutical microparticles. In another embodiment, the amount of one or more fatty acids sufficient to provide said mixture in substantially homogenous form is about 52 wt. % of the pharmaceutical composition or the pharmaceutical microspheres.

In one embodiment, the pharmaceutical composition of the present disclosure further comprises pharmaceutically acceptable excipients.

In one embodiment, suitable pharmaceutically acceptable excipients include fats and fatty substances. Examples of fats and fatty substances include fatty alcohols (such as lauryl, myristyl stearyl, cetyl or cetostearyl alcohol), fatty acid derivatives, including but not limited, fatty acid esters, fatty acid glycerides (mono-, di- and tri-glycerides), fatty amines, and hydrogenated fats. Specific examples include, but are not limited to hydrogenated vegetable oil, hydrogenated cottonseed oil, hydrogenated castor oil, hydrogenated oils available under the trade name Sterotex®, cocoa butter, glyceryl behenate (available under the trade name COMPRITOL 888®), glyceryl dipalmitostearate (available under the trade name PRECIROL®), and stearyl alcohol.

In some embodiments, drug containing multiparticulates are coated. Drug containing multiparticulates can be coated with water insoluble materials, slowly water soluble materials, organic insoluble materials and/or materials with pH dependent solubilities. In general, any coating procedure which provides a contiguous coating on each multiparticulate can be used. Coating procedures known in the arts include, but are not limited to, fluid bed coating processes and microencapsulation. Detailed descriptions of these processes can be found in "Remington—The science and practice of pharmacy", 20th Edition, Jennaro et al., (Phila, Lippencott, Williams, and Wilkens, 2000.

The water-insoluble coating materials may be selected from natural or synthetic film-formers used alone, in admixture with each other, or in admixture with plasticizers, pigments and other substances to alter the characteristics of the coating. A water-insoluble but water-permeable diffusion barrier may contain ethyl cellulose, methyl cellulose and mixtures thereof. The water-permeable diffusion barrier may also include ammonio methacrylate copolymers sold under the trade name EUDRAGIT®. (Rohm Pharma), such as EUDRAGIT RS, EUDRAGIT RL, EUDRAGIT NE and mixtures thereof. Other synthetic polymers, for example, polyvinyl acetate (available under the trade name KOLLICOAT®), can also be used to form water-insoluble but permeable coatings.

Coating materials may also include one or more pH sensitive polymers which are insoluble in the acid environment of the stomach, and soluble in the more basic environment of the GI tract. These coatings, referred to as enteric coatings, create a dosage form designed to prevent drug release in the stomach.

Enteric coated particles can be prepared as described in "Pharmaceutical dosage form tablets", eds. Liberman et. al. (New York, Marcel Dekker, Inc., 1989), "Remington—The science and practice of pharmacy", 20th ed., Lippincott Williams & Wilkins, Baltimore, Md., 2000, and "Pharmaceutical dosage forms and drug delivery systems", 6th Edition, Ansel et. al., (Media, Pa.: Williams and Wilkins, 1995). Examples of suitable coating materials include, but are not limited to, cellulose polymers, such as cellulose acetate phthalate, hydroxypropyl cellulose, hydroxypropyl methylcellulose phthalate and hydroxypropyl methylcellulose acetate succinate; polyvinyl acetate phthalate, acrylic acid polymers and copolymers, and certain methacrylic resins that are commercially available under the trade name EUDRAGIT®. (Rohm Pharma). Additionally the coating material may contain conventional carriers such as plasticizers, pigments, colorants, glidants, stabilization agents, and surfactants.

In some embodiments, drug containing multiparticulates are blended with extragranular material and filled into hard shell capsules. The extragranular material can serve several functions. One or more extragranular materials, such as lubricants or glidants, can be used to reduce the tendency of the multiparticulates from agglomerating or to provide better flow properties to the formulation. Examples of suitable materials for this purpose include, but are not limited to, magnesium stearate, zinc stearate, colloidal silicone dioxide, talc, starch, calcium stearate, hydrogenated vegetable oils, stearic acid, sodium stearyl fumarate, sodium benzoate, sodium acetate, leucine, sodium oleate, sodium lauryl sulfate, magnesium lauryl sulfate and polyethylene glycol. In one embodiment, the pharmaceutically acceptable excipients include, but are not limited to, silicon dioxide colloidal and magnesium stearate. In other embodiments, the extragranular material is a natural or synthetic gel forming excipient, added to form a gel or viscous environment around the particles when exposed to an aqueous environment. Extragranular material of this type can be used to modulate the release of drug from the dosage form when the dosage form is manipulated (for example for preparation for IV abuse), or in some embodiments when the dosage form is administered intact.

In some embodiments, the compositions are coated with an enteric coating. Enteric coatings known in the art are applied directly to the abuse-deterrent multiparticulate or coated multiparticulate compositions or are applied to the surface of a capsule or tablet containing the abuse deterrent multiparticulate and/or coated multiparticulate compositions. Enteric coatings known in the art include, for example, acrylic polymers that are commercially available under the trade name EUDRAGIT®, cellulose acetate phthalate, hydroxypropylmethyl-cellulose phthalate, polyvinylacetate phthalate, shellac, hydroxypropyl-methylcellulose succinate, cellulose acetate trimellitate or mixtures thereof. In one embodiment, the particles are coated with cellulose acetate phthalate.

Dosage forms can include one or more drugs. When the dosage form includes two or more drugs they can be Scheduled drugs or can be a combination of Scheduled and non-Scheduled drugs. The drugs can be incorporated into the same multiparticulates. Alternatively, the drugs can be incorporated into separate multiparticulate compositions where the Scheduled drugs are incorporated into abuse deterrent multiparticulate compositions and the non-Scheduled drugs are incorporated into abuse deterrent multiparticulate compositions, sustained release compositions known in the art or immediate release compositions known in the art. The compositions containing the different drugs can be formulated into a single solid dosage form suitable for oral administration; for example, they can be incorporated into a hard capsule shell, or combined with appropriate excipients and compressed into a tablet form.

Examples of non-scheduled drugs that may be included in dosage forms described herein include, but are not limited to, aspirin, acetaminophen, non-steroidal anti-inflammatory drugs, cyclooxygenase II inhibitors, N-methyl-D-aspartate receptor antagonists, glycine receptor antagonists, triptans, dextromethorphan, promethazine, fiorinal, guaifenesin, butalbital, and caffeine.

In some embodiments, the contemplated compositions comprising a plurality of multiparticulates comprise one or more additional excipients that are combined with the multiparticulates. The one or more additional excipients comprise diluents, lubricants, gel forming excipients, and combinations thereof. In other embodiments, each multiparticulate comprises optional excipients including, but are not limited to diluents, binders, lubricants, disintigrants, colorants, plasticizers and the like.

Diluents, also termed "fillers," are typically necessary to increase the bulk of a solid dosage form so that a practical size is provided for compression of tablets. Examples of diluents include cellulose, dry starch, microcrystalline cellulose, dicalcium phosphate, calcium sulfate, sodium chloride confectioner's sugar, compressible sugar, dextrates, dextrin, dextrose, sucrose, mannitol, powdered cellulose, sorbitol, and lactose.

Binders are used to impart cohesive qualities powdered materials and can include materials such as starch, gelatin, sugars, natural and synthetic gums, polyethylene glycol, ethylcellulose, methylcellulose, hydroxypropylmethyl-cellulose, carboxymethylcellulose, waxes and polyvinyl pyrrolidone.

Lubricants are used to facilitate tablet and capsule manufacture. Examples of lubricants include talc, magnesium stearate, zinc stearate, calcium stearate, hydrogenated vegetable oils stearic acid, sodium stearyl fumarate, sodium benzoate, sodium acetate, leucine, sodium oleate, sodium lauryl sulfate, magnesium lauryl sulfate and polyethylene glycol.

Disintegrants can be added to pharmaceutical formulations in order to facilitate "breakup" or disintegration after administration. Materials used for this purpose include starches, clays, celluloses, aligns, gums, and cross-linked polymers.

A plasticizer may be included in coating materials to alter their mechanical properties. Examples of plasticizers include benzyl benzoate, chlorobutanol, dibutyl sebacate, diethyl phthalate, glycerin, mineral oil, polyethylene glycol, sorbitol, triacetin, triethyl citrate, glycerol, etc.

One or more surfactants may also be added to the final dosage form to modulate the release of drug from the multiparticulate composition. Examples include, but are not limited to, lecithin, sodium dodecyl sulfate, poloxamer, Cremophor, polysorbates, and polyoxyglycerides.

In addition to the additives above, coloring and flavoring agents may also be incorporated into the composition. Selection of excipients and the amounts used may be readily determined by the formulation scientist based upon experience and consideration of standard procedures and reference works in the field.

In one embodiment, the cured microparticles or cured formulated microparticles of the present disclosure exhibit a change in the mean percent drug released at the 4 hour dissolution time point after storage for 6 months at 25° C. and 60% RH that is within about 15%, about 10%, about 5%, or about 2.5%, when dissolution is conducted using USP Apparatus I in pH 4.5 sodium acetate buffer supplemented with 0.03% Tween 20. In one embodiment, the cured microparticles or cured formulated microparticles of the present disclosure exhibit a change in the mean percent drug released at the 4 hour dissolution time point after storage for 6 months at 25° C. and 60% RH within about 15%, 14%, 13%, 12%, 11%, 10%, 9.5%, 9%, 8.5%, 8%, 7.5%, 7%, 6.5%, 6%, 5.5%, 5%, 4.5%, 4%, 3.5%, 3%, 2.5%, 2%, or 1.5%.

In one embodiment, the pharmaceutical composition of the present disclosure provides an extended-release of the drug upon administration.

Process for Making the Pharmaceutical Compositions

The present disclosure provides a process of making a pharmaceutical composition designed to reduce the potential for improper administration of drugs that are subject to abuse. In one embodiment, the process involves forming drug containing microparticles. In another embodiment, the process involves a curing step which provides improved dissolution stability of the pharmaceutical compositions.

In one embodiment, the process of the present disclosure for making the pharmaceutical composition comprises the steps of: a) mixing one or more drugs, one or more pharmaceutically acceptable waxes, and one or more pharmaceutically acceptable fatty acids at a temperature sufficient to form a substantially homogeneous melt; b) forming solid microparticles from the substantially homogeneous melt; c) optionally further formulating the solid microparticles with additional pharmaceutically acceptable excipients, and d) curing the solid microparticles or formulated microparticles at one or more temperatures within the range of 25° C. up to and including the inversion temperature, for a minimum of about 48 hours.

Step (a) can comprise any suitable method of combining one or more fatty acids, one or more drugs, and one or more pharmaceutically acceptable waxes, in any order, at a temperature sufficient to form a substantially homogenous melt comprising fatty acid salts dissolved, at least in part, in the one or more pharmaceutically acceptable waxes. By way of non-limiting examples, the one or more drugs, the one or more fatty acids and the one or more pharmaceutically acceptable fatty acids can be combined together at a temperature sufficient to form a substantially homogeneous melt; alternatively the one or more drugs can first be reacted with one or more fatty acids to form fatty acid salts of the one or more drugs, then combined with the one or more pharmaceutically acceptable waxes and, optionally, one more other excipients, at a temperature sufficient to form a substantially homogeneous melt; or alternatively the one or more fatty acids, the one or more drugs, the one or more pharmaceutically acceptable waxes, and, optionally, the one or more other excipients, can be combined sequentially in any order at a temperature sufficient to form a substantially homogeneous melt, etc. Any combination or permutation of combining the one or more fatty acids, one or more drugs, and one or more pharmaceutically acceptable waxes and excipients is acceptable provided that the end result is the formation of a substantially homogeneous melt comprising a fatty acid salt homogeneously dispersed, at least in part, in the pharmaceutically acceptable wax(es).

In a further embodiment, the microparticles disclosed herein can further comprise an additional phase dispersed therein. This additional phase can include solid excipients, such as pore formers, surfactants, anti-static agents, anti-tack agents, lubricants, fillers etc. However, the fatty acid salts or complexes of the one or more drugs are substantially homogeneously dispersed or dissolved in the pharmaceutically acceptable wax(es).

In one embodiment, the minimum temperature sufficient to form a substantially homogeneous melt in step a) is about 50° C. In one embodiment, the minimum temperature sufficient to form a substantially homogeneous melt is about 60° C. In another embodiment, the minimum temperature sufficient to form a substantially homogeneous melt is about 70° C. In another embodiment, the minimum temperature sufficient to form a substantially homogeneous melt is about 80° C. In some embodiments, the temperature sufficient to form a substantially homogeneous melt is experimentally determined by slowly increasing the temperature with mixing. In some embodiments the substantially homogeneous melt is a true solution in which all components are in a liquid or dissolved state.

In one embodiment of the process disclosed herein, forming solid microparticles from the substantially homogeneous melt in step b) is carried out by feeding the melt from step a) onto a spinning disk. For example, the substantially homogeneous melt can be pumped (e.g., with a gear pump) through a heated feed line which dispenses the melt onto a rapidly spinning disk (e.g., a spinning disk atomizer), at a speed sufficient to break the melt into a spray of droplets of the desired particle size range. The droplets rapidly solidify and are collected in an enclosure to provide suitable particles, e.g. microparticles. The process may result in substantially spherical particles in which case they may be referred to as microspheres. Sieving of microparticles to produce the desired size range may also be carried out.

In other embodiments, step b) is carried out by spraying the melt from step a) using any number of congealing devices, including an ultrasonic nozzle, a pressure nozzle or a 2-fluid nozzle. Spray configurations may include top down configurations and fountain configurations whereby the melt is sprayed and atomized in an upward direction. Standard enclosures for collection of the solid microparticles include stainless steel and pharmaceutically acceptable plastic vessels and enclosures.

In other embodiments solid microparticles are formed from an extrusion process. In yet a further embodiment, solid microparticles are formed by solidifying the melt into a solid slab and subsequently milling to form suitable microparticles. Sieving of microparticles to produce the desired size range may also be carried out. Other processes, known in the pharmaceutical arts, may be used to produce microparticles of a desired size distribution from the hot melt.

The microparticles of the present invention are characterized by a median particle size of less than about 3000 microns. In some embodiments the microparticles are characterized by a median particle size of less than about 1000 microns. In some embodiments the microparticles of the present invention are characterized by a median particle size of less than about 700 microns, about 600 microns, about 500 microns, about 400 microns, about 300 microns or about 200 microns, inclusive of all values, ranges, or subranges therebetween. In some embodiments the microparticles of the present invention are characterized by a median particle size of about 300 microns.

As described herein, the term "curing" refers to heating or maintaining the compositions of the present invention at defined temperature(s) for a defined period of time as described herein.

Curing, as described herein, can be carried out at any time after preparation of the microparticles. For example, the curing steps described herein may be conducted on microparticles directly, or may be conducted on microparticles that have been further formulated. In addition, curing can be carried out on the finished unit dosage form, e.g., formulated or unformulated microparticles filled into capsules or compressed into a tablet. For example, in some embodiments microparticles are blended or formulated with external excipients, and the curing is conducted on the blended or formulated microparticles. In other embodiments the blended or formulated microparticles may be further encapsulated prior to curing. In yet further embodiments the blended microparticles may be compressed into tablets prior to curing.

In one embodiment of the process disclosed herein, curing the solid microparticles or formulated microparticles in step c) is carried out by a single-stage curing process, by a 2-stage curing process, or by a multi-stage process. In the single-stage curing process the solid microparticles are held at a single temperature that is at or below the inversion temperature for an appropriate time as experimentally determined. A 2-stage curing process utilizes two different curing temperatures for appropriate time(s) as experimentally determined. A 3-stage curing process utilizes three curing temperatures, wherein the first and the third may be same or different. A 4-stage curing process utilizes four curing temperatures, wherein non-consecutive stages can have the same or different temperatures, e.g., the first and the third or the first and the fourth. Additional curing stages can be applied as needed. A gradual temperature ramp may also be applied over time. However, at least one stage should be carried out at a temperature at or below the inversion temperature, for a time sufficient to reduce the change in the dissolution profile after storing for 6 months at 25° C. and 60% RH when compared to otherwise identical uncured microparticles after storing for 6 months at 25° C. and 60% RH.

In one embodiment, the process disclosed herein requires a 1-stage curing process. In another embodiment, the process disclosed herein requires a 2-stage curing process.

In one embodiment of the process disclosed herein, curing the solid microparticles takes place at a temperature within the range of 25° C. up to and including the inversion temperature. In another embodiment, the curing process takes place at a temperature falling within the range between 25° C. to about 60° C. or from 25° C. to about 50° C. or from about 25° C. to about 36° C., or from about 30° C. to about 45° C. In one embodiment of the disclosed process, the curing takes place at about 25, 26, 27, 28, 29, 30, 31, 32, 33, 34, 35, 36, 37, 38, 39, 40, 41, 42, 43, 45, 46, 47, 48, 49, 50, 51, 52, 53, 54, 55, 56, 57, 58, 59, or about 60° C.

In one embodiment, the inversion temperature is about 34, 35, 36, 37, or 38° C. In some embodiments, the curing process disclosed herein is a 2-stage process which involves heating the microparticles to a first temperature above the inversion temperature and subsequently a second temperature at or below the inversion temperature.

In one embodiment, the 2-stage curing process is carried out at a first temperature of about 37, 38, 39, 40, 41, or 42° C. and a second temperature of about 28, 29, 30, 31, 32, 33, 34, 35, or 36° C. In one embodiment, the 2-stage curing process is carried out at a first temperature of about 40° C. and a second temperature of about 30° C. In another embodiment, the 2-stage curing process is carried out at a first temperature of about 38° C. and a second temperature of about 32° C.

In one embodiment of the process disclosed herein, the time sufficient for curing is the time required to reduce the change in the dissolution profile for cured compositions after storing for 6 months at 25° C. and 60% RH when compared with the change observed for otherwise identical uncured compositions after storing for 6 months at 25° C. and 60% RH when dissolution is conducted using USP Apparatus I in pH 4.5 sodium acetate buffer supplemented with 0.03% Tween 20. This time can be determined experimentally. To do this, a baseline change for the uncured composition must be established by comparing the dissolution profile for the uncured composition at the time of manufacture with the dissolution profile following storage for 6 months at 25° C. and 60% RH. The goal of curing is to improve upon, or reduce, this uncured baseline change. To determine the appropriate curing time, the same composition should be cured at a temperature between 25° C. and the inversion temperature, for various times. Subsequently, the dissolution profile of the cured composition at the time of manufacture should be compared with the dissolution profile following storage for 6 months at 25° C. and 60% RH. An appropriate time is established when the change in the cured composition following storage is less than the corresponding change for the uncured composition. In another embodiment, the time sufficient for curing is a minimum of about 48 hours. In one embodiment, the time sufficient for curing is about 2, 3, 4, 5, 6, 7, 8, 9, 10, 11, 12, 13, 14, 15, 16, 17, 18, 19, 20, 21, 22, 23, 24, 25, 26, 27, 28, 29, 30, or 31 days. In some embodiments, the time sufficient for curing is about 7 days.

In one embodiment of the process disclosed herein, the time sufficient for curing is the total time, e.g., combined time cured at first temperature and second temperature in a multi-stage curing process.

In embodiment, the cured microparticles or cured formulated microparticles prepared by the disclosed process exhibit a change in the mean percent drug released at the 4 hour dissolution time point after storage for 6 months at 25° C. and 60% RH that is less than about 15%, about 10%, about 5%, or about 2.5%, when dissolution is conducted using USP Apparatus I in pH 4.5 sodium acetate buffer supplemented with 0.03% Tween 20. In one embodiment, the cured microparticles or cured formulated microparticles of the present disclosure exhibit a change in the mean percent drug released at the 4 hour dissolution time point after storage for 6 months at 25° C. and 60% RH within about 15%, 14%, 13%, 12%, 11%, 10%, 9.5%, 9%, 8.5%, 8%, 7.5%, 7%, 6.5%, 6%, 5.5%, 5%, 4.5%, 4%, 3.5%, 3%, 2.5%, 2%, or 1.5%.

In one embodiment of the present disclosure, a pharmaceutical composition prepared by any one of the processes disclosed herein is provided. In another embodiment of the present disclosure, a capsule comprising a pharmaceutical composition prepared by any one of the processes disclosed herein is provided.

In a further embodiment of the present disclosure, a pharmaceutical composition comprising oxycodone and myristic acid prepared by any one of the processes disclosed herein is provided where the inversion temperature is about 36° C. In another embodiment of the present disclosure, a capsule comprising a pharmaceutical composition comprising oxycodone and myristic acid prepared by any one of the processes disclosed herein is provided where the inversion temperature is about 36° C.

Method of Treatment

The present disclosure provides a method of administering any one of the pharmaceutical compositions or a capsule as disclosed herein to a subject in need thereof. In some embodiments, the method includes treatment or management of pain. In one embodiment, the pain to be treated can be severe enough to require daily, around-the-clock, long-term opioid treatment and for which alternative treatment options are inadequate. In one embodiment, the disclosed method provides a therapeutically effective amount of the one or more drugs to a subject in need thereof.

For the purposes of this disclosure, the composition of the present disclosure can be formulated for administration by a variety of means. In one embodiment, the administration of the method disclosed herein is orally. In one embodiment, a solid oral dosage form, such as a capsule can be used to administer to a subject in need thereof.

EXAMPLES

Material and Methods

Unless otherwise noted, the following material and equipment were used as received or under standard operating conditions. Laboratory ovens and/or stability chambers were used to cure microspheres. Unless otherwise noted, a manual encapsulator or an automated encapsulator was used to fill capsules with blend.

Microparticles

Excipients were first melted in a stainless steel jacketed vessel. The active pharmaceutical ingredient (API) was dissolved in the melt with stirring. The melt was then processed into microspheres by one of the following procedures:

A) The melt was fed to a spinning disk. The disk rotates at a speed designed to produce solid microspheres of the desired particle size distribution.

B) The melt was forced through a plastic atomization nozzle mounted on a plastic syringe. The syringe plunger was pressed through the barrel using a pneumatic piston.

The piston was activated with an air pressure sufficient to press the melt through the barrel at a speed high enough to atomize the melt and produce microspheres.

Curing, blending and encapsulation (where applicable) were carried out as noted in the individual examples.

Dissolution Test

Product dissolution is conducted using USP Apparatus with media (900 mL, pH 4.5 sodium acetate buffer, 0.03% Tween 20) pre-heated to 37° C. For capsule dissolution, USP Apparatus I (baskets) at 100 rpm was utilized.

Example 1: Stability of Uncured Microspheres at Different Conditions of Temperature and Humidity Microspheres containing oxycodone, myristic acid, beeswax, carnauba wax and stearoyl polyoxyl-32 glycerides were produced using spinning disk atomization as described above. The microspheres were blended with colloidal silicon dioxide and magnesium stearate and machine encapsulated to form capsules. Capsules were packaged in high-density polyethylene bottles and placed in stability chambers according to ICH conditions; long-term (25° C./60% RH), intermediate (30° C./65% RH) and accelerated (40° C./75% RH) conditions were used in the study. The dissolution profile of the capsules was determined at the time of manufacture and periodically while on stability. The % drug released as a function of time in dissolution is shown in FIG. 1 at time zero and after storage for 3 months at all 3 ICH stability conditions.

The behavior of the microspheres was unexpected on stability. The dissolution profile of the uncured microspheres tends to increase (i.e., faster dissolution) on storage at 40° C./75% RH and decrease (i.e., slower dissolution) on storage at 25° C./60% RH or 30° C./65% RH. Given that the microspheres are hydrophobic and absorb virtually no moisture irrespective of humidity level, i.e. dissolution is not impacted by humidity level, the data suggests the presence of an "inversion temperature", between 30° C. and 40° C., at which the dissolution behavior reverses and rather than tending to decrease, will tend to increase. Furthermore, the decrease observed at long-term conditions (predictive of long-term room temperature storage in a warehouse, pharmacy or medicine cabinet) is greater than desired after 3 months (eg, approximately 15% lower at the 4 hour dissolution time point).

Example 2: Establishment of Inversion Temperature

On the basis of stability data shown in Example 1, the dissolution behavior of microspheres containing oxycodone, myristic acid, beeswax, carnauba wax and stearoyl polyoxyl-32 glycerides was investigated at temperatures falling between 30° C. and 40° C. Specifically, the microspheres were exposed to elevated temperatures between 32° C.-36° C. after 2 days (48 hours) and 6-7 days. FIGS. 2A and 2B display the impact of curing temperature at each individual dissolution time point. FIG. 2A shows the impact of curing for 2 days and FIG. 2B shows the impact of curing for 6-7 days. Both graphs also show the dissolution results for the uncured formulation as a control. After 2 days of curing at 32° C.-34° C., there is only a slight reduction in dissolution versus the uncured formulation. A further drop in dissolution is generally observed with increasing temperature from 34° C. to 36° C., especially at the 8-hour and longer time points.

Changes after 6-7 days of curing are not linear with temperature. After curing for 7 days at 32° C., dissolution decreases significantly below the dissolution of uncured material. Dissolution of uncured formulation at the 2-hour, 4-hour, 8-hour and 12-hour dissolution time points is 30.7%, 48.1%, 68.2%, and 83.2%, respectively. The corresponding dissolution after curing for 7 days at 32° C. is 27.3%, 42.04%, 60.3%, and 75.5%, respectively. After curing at 33° C. or 34° C., dissolution remained below that of uncured material. The dissolution is minimal around 35° C. where it was now lower than at 32° C. The slowest dissolution rate was thus observed after 7 days at 35° C.; however, there was an abrupt change in behavior between 35° C. and 36° C., with the dissolution starting an increase to a level that is higher than the dissolution of uncured control material.

The behavior between 32° C. and 36° C. was qualitatively consistent with that observed in FIG. 1, i.e. dissolution decreases at low curing temperatures and increases at high curing temperatures; however, between these temperatures the dissolution behavior was non-linear and exhibited an inflection point around approximately 36° C. This is defined as the "inflection or inversion temperature". This explains the observed increase in dissolution in Example 1 with storage at 40° C., above the inversion temperature.

Example 3: Single-Stage Curing Process

Based on the dissolution behavior for microspheres containing oxycodone, myristic acid, beeswax, carnauba wax and stearoyl polyoxyl-32 glycerides after exposure to different temperatures, studies to implement a curing process were conducted. The hypothesis was that curing at a temperature above 25° C., but below the inversion temperature (35-36° C.), would improve the dissolution stability of the microspheres when stored at ICH long-term conditions (25° C./75% RH). The process consisted of a single-stage (ie, a single temperature) and a duration of 30 days. For these studies, microspheres were blended with colloidal silicon dioxide and magnesium stearate and encapsulated prior to curing. Uncured microspheres that were similarly blended and encapsulated were also tested as a control.

The dissolution stability behavior of uncured capsules that were stored at 25° C./60% RH is shown in FIG. 3A. A relatively large drop in dissolution is observed. Dissolution drops by 15% at the 4-hour time point on storage for 6 months at 25° C./60% RH.

The dissolution stability behavior of capsules that were cured at 34° C., 30° C., or 32° C. and then stored at 25° C./60% RH for 6 month is shown in FIG. 3B, FIG. 3C, and FIG. 3D, respectively. Curing below the inversion temperature (34° C., 32° C., and 30° C.) results in considerably more stable product than no curing (compare to FIG. 3A).

Example 4: Two-Stage Curing Process

A 2-stage curing process was also tested. In the 2-stage curing process, the product is held first at a relatively high temperature above the inversion temperature followed by temperature below the inversion temperature.

A 2-stage curing process which consists of holding the microspheres at 40° C. for 4 days followed by a period of 3 days at 30° C. was evaluated (40° C./4d; 30° C./3d). These conditions were applied to the uncured microspheres of Example 3, followed by blending with colloidal silicon dioxide and magnesium stearate, and encapsulation. The capsules were tested for dissolution at time zero and following storage for 6 months at 25° C./60% RH. Comparison of data in FIGS. 3E and 3A show that curing for 4 days at 40° C. followed by 3 days at 30° C. results in a more stable formulation versus uncured formulation stored for 6 months at 25° C./60% RH.

Table 1 summarizes the difference in dissolution between time zero (i.e., measured after manufacture) and after 6 months of storage at 25° C. and 65% RH for Example 3 compositions. As shown in the table, the difference is reduced for all curing conditions relative to the microsphere formulation that was not subjected to curing (control condition). For example, at the 4 hour dissolution time point the difference is reduced by at least half for all curing conditions.

TABLE 1

Change in dissolution
(% Released at Time Zero - % Released after 6 months at 25° C./65% RH)

| Dissolution Time Point (hours) | Control- No Curing | Curing at 30° C. (1 month) | Curing at 32° C. (1 month) | Curing at 34° C. (1 month) | Curing at 36° C. (1 month) | Curing at 40° C. (4 days), 30° C. (3 days) |
|---|---|---|---|---|---|---|
| 1 | 8.4 | 0.6 | −0.4 | 1.5 | 2.3 | 6.0 |
| 2 | 11.0 | 1.6 | 0.2 | 2.0 | 4.4 | 7.1 |
| 4 | 14.7 | 2.3 | 0.2 | 3.0 | 6.1 | 7.0 |
| 8 | 15.5 | 3.0 | 0.3 | 3.3 | 6.8 | 6.3 |
| 12 | 13.4 | 2.8 | 0.2 | 3.3 | 7.4 | 4.6 |
| 16 | 9.4 | 3.1 | 0.6 | 3.1 | 2.1 | 5.9 |
| 20 | 5.1 | 2.9 | 0.01 | 3.4 | 1.5 | −0.4 |
| 24 | 2.6 | 2.6 | −0.8 | 2.4 | 2.6 | −3.0 |

Example 5: Inversion Temperature for Formulations Comprising Drug, Stearic acid, and Waxes The dissolution behavior of a microsphere formulation comprising oxycodone, stearic acid and waxes before and after single stage curing at 50° C. is shown in FIG. 4A. Dissolution decreases when the formulation is cured at 50° C.

The dissolution behavior of a microsphere formulation comprising oxymorphone, stearic acid and waxes before and after curing at 50° C. is shown in FIG. 4B. Here again, dissolution decreases when curing at 50° C.

The dissolution behavior of a microsphere formulation comprising oxymorphone, stearic acid and waxes before and after curing at 55° C. or 60° C. is shown in FIG. 4C. Dissolution increases when curing at 55° C. or 60° C. FIG. 4A, FIG. 4B, and FIG. 4C indicate that the inversion temperature is between 50° C. and 55° C. when using stearic acid. These results indicate that the inversion temperature can increase with increasing fatty acid molecular weight or with a change in the formulation.

INCORPORATION BY REFERENCE

All references, articles, publications, patents, patent publications, and patent applications cited herein are incorporated by reference in their entireties for all purposes. However, mention of any reference, article, publication, patent, patent publication, and patent application cited herein is not, and should not be taken as acknowledgment or any form of suggestion that they constitute valid prior art or form part of the common general knowledge in any country in the world.

What is claimed is:

1. A process comprising:
    a. preparing a mixture comprising:
        (i) oxycodone, myristic acid, beeswax and carnauba wax, or
        (ii) oxycodone in the form of a fatty acid salt, beeswax and carnauba wax at a temperature sufficient to form a substantially homogeneous melt;
    b. forming solid microparticles from the substantially homogeneous melt;
    c. optionally further formulating the solid microparticles with additional pharmaceutically acceptable excipients, and
    d. curing the solid microparticles or formulated microparticles at a temperature within the range of 25° C. up to and including the inversion temperature, for a minimum of about 48 hours.

2. The process of claim 1, wherein the cured formulated microparticles exhibit less change in the dissolution profile after storage for 6 months at 25° C. and 60% RH than otherwise identical uncured formulated microparticles after storage for 6 months at 25° C. and 60% RH,
    wherein dissolution is conducted at 100 RPM using USP Apparatus I in 900 mL of pH 4.5 sodium acetate buffer supplemented with 0.03% Tween 20 at 37° C.

3. The process of claim 1, wherein the cured microparticles or cured formulated microparticles exhibit less than a 15% change in the mean percent drug released at the 4 hour dissolution time point after storage for 6 months at 25° C. and 60% RH, and
    wherein dissolution is conducted using USP Apparatus I in pH 4.5 sodium acetate buffer supplemented with 0.03% Tween 20.

4. The process of claim 1, wherein the cured microparticles or cured formulated microparticles exhibit less than a 10% change in the mean percent drug released at the 4 hour dissolution time point after storage for 6 months at 25° C. and 60% RH, and
    wherein dissolution is conducted using USP Apparatus I in pH 4.5 sodium acetate buffer supplemented with 0.03% Tween 20.

5. The process of claim 1, wherein the cured microparticles or cured formulated microparticles exhibit less than a 5% change in the mean percent drug released at the 4 hour dissolution time point after storage for 6 months at 25° C. and 60% RH, and
    wherein dissolution is conducted using USP Apparatus I in pH 4.5 sodium acetate buffer supplemented with 0.03% Tween 20.

6. The process of claim 1, wherein the cured microparticles or cured formulated microparticles exhibit less than a 2.5% change in the mean percent drug released at the 4 hour dissolution time point after storage for 6 months at 25° C. and 60% RH, and wherein dissolution is conducted using USP Apparatus I in pH 4.5 sodium acetate buffer supplemented with 0.03% Tween 20.

7. The process of claim 1, wherein the inversion temperature is approximately 36° C.

8. The process of claim 1, wherein the microparticles or formulated microparticles are cured at a first temperature above the inversion temperature and subsequently a second temperature below the inversion temperature.

9. A pharmaceutical composition prepared by the process of claim 1.

10. The pharmaceutical composition of claim 9, comprising about 9 mg to about 72 mg oxycodone or an equivalent amount of fatty acid salt thereof.

11. The pharmaceutical composition of claim 9, comprising about 9 mg to about 36 mg oxycodone or an equivalent amount of a fatty acid salt thereof.

12. The pharmaceutical composition of claim 9, comprising myristic acid in about 30 wt. % to about 70 wt. % of the pharmaceutical composition.

13. The pharmaceutical composition of claim 9, comprising myristic acid in about 40 wt. % to about 60 wt. % of the pharmaceutical composition.

14. The pharmaceutical composition of claim 9, wherein the combination of beeswax and carnauba wax comprises about 20 wt. % to about 60 wt. % of the pharmaceutical composition.

15. The pharmaceutical composition of claim 9, wherein the combination of beeswax and carnauba wax comprises about 30 wt. % to about 50 wt. % of the pharmaceutical composition.

16. The pharmaceutical composition of claim 9, comprising:
   a. about 9 mg to about 72 mg oxycodone or an equivalent amount of a fatty acid salt thereof;
   b. about 30 wt. % to about 70 wt. % of myristic acid; and
   c. about 20 wt. % to about 60 wt. % of a combination of beeswax and carnauba wax.

17. The pharmaceutical composition of claim 9, comprising:
   a. about 9 mg to about 72 mg oxycodone or an equivalent amount of a fatty acid salt thereof;
   b. about 40 wt. % to about 60 wt. % of myristic acid; and
   c. about 30 wt. % to about 50 wt. % of a combination of beeswax and carnauba wax.

18. The pharmaceutical composition of claim 9, comprising:
   a. about 9 mg to about 36 mg oxycodone or an equivalent amount of a fatty acid salt thereof;
   b. about 40 wt. % to about 60 wt. % of myristic acid; and
   c. about 30 wt. % to about 50 wt. % of a combination of beeswax and carnauba wax.

19. A capsule comprising the pharmaceutical composition of claim 9.

20. A capsule comprising the pharmaceutical composition of claim 16.

21. A capsule comprising the pharmaceutical composition of claim 17.

22. A capsule comprising the pharmaceutical composition of claim 18.

23. Pharmaceutically acceptable solid microparticles or formulated microparticles comprising: a mixture prepared from a homogeneous melt comprising beeswax, carnauba wax, oxycodone or a myristate salt of oxycodone, and a sufficient amount of myristic acid to provide said microparticles in substantially homogeneous form; wherein said microparticles or formulated microparticles are cured at one or more temperatures within the range of 25° C. up to and including the inversion temperature, for a minimum of about 48 hour.

24. A method of treating pain comprising administering the pharmaceutical composition of claim 9 to a patient in need thereof.

25. A method of treating pain comprising administering the pharmaceutical composition of claim 16 to a patient in need thereof.

26. A method of treating pain comprising administering the pharmaceutical composition of claim 18 to a patient in need thereof.

27. A method of treating pain comprising administering the capsule of claim 19 to a patient in need thereof.

28. A method of treating pain comprising administering the capsule of claim 20 to a patient in need thereof.

29. A method of treating pain comprising administering the capsule of claim 22 to a patient in need thereof.

30. A method of treating pain comprising administering the pharmaceutically acceptable microparticles or formulated microparticles of claim 23 to a patient in need thereof.

* * * * *